US007941215B2

(12) United States Patent
Lapanashvili

(10) Patent No.: US 7,941,215 B2
(45) Date of Patent: May 10, 2011

(54) ELECTROTHERAPY APPARATUS AND METHOD OF TREATING A PERSON OR A MAMMAL USING SUCH ELECTROTHERAPY APPARATUS

(75) Inventor: Larry Lapanashvili, Winterthur (CH)

(73) Assignee: CardioLa Ltd., Winterthur (CH)

(*) Notice: Subject to any disclaimer, the term of this patent is extended or adjusted under 35 U.S.C. 154(b) by 1060 days.

(21) Appl. No.: 10/578,596

(22) PCT Filed: Nov. 8, 2004

(86) PCT No.: PCT/EP2004/012619
§ 371 (c)(1),
(2), (4) Date: Mar. 6, 2007

(87) PCT Pub. No.: WO2005/044374
PCT Pub. Date: May 19, 2005

(65) Prior Publication Data
US 2007/0156178 A1 Jul. 5, 2007

Related U.S. Application Data

(60) Continuation-in-part of application No. 10/994,981, filed on Nov. 19, 2004, now abandoned, which is a division of application No. 10/069,333, filed as application No. PCT/EP00/07933 on Aug. 14, 2000, now Pat. No. 6,832,982, which is a continuation-in-part of application No. 09/378,181, filed on Aug. 20, 1999, now Pat. No. 6,450,942.

(30) Foreign Application Priority Data

Nov. 7, 2003 (EP) .................................. 03025662

(51) Int. Cl.
*A61N 1/37* (2006.01)

(52) U.S. Cl. .............................................. 607/9; 607/11
(58) Field of Classification Search .................. 607/9, 11
See application file for complete search history.

(56) References Cited

U.S. PATENT DOCUMENTS

| 3,983,881 A * | 10/1976 | Wickham ........................ 607/43 |
| 4,541,417 A * | 9/1985 | Krikorian ....................... 600/17 |
| 5,257,623 A * | 11/1993 | Karasev et al. ................. 607/27 |
| 2004/0082979 A1 * | 4/2004 | Tong et al. ...................... 607/48 |

FOREIGN PATENT DOCUMENTS

| WO | WO 01/13990 A1 | 3/2001 |
| WO | WO 03/020364 A2 | 3/2003 |

* cited by examiner

*Primary Examiner* — Scott M Getzow
*Assistant Examiner* — Joseph M Dietrich
(74) *Attorney, Agent, or Firm* — Kilpatrick Townsend & Stockton LLP

(57) ABSTRACT

An electrotherapy apparatus comprising a sensor for detecting periodically recurring signal peaks, in particular the R-R peaks of an electrocardiogram of a person, a processor for deriving from the time interval between said periodically recurring signal peaks a time delay corresponding to approximately the end of the T-wave, and a trigger system initiated by an output signal of said processor or embodied within said processor for applying electrical stimulations to one or more active electrodes provided on the said person at a time related to the end of said time delay. The processor is adapted to generate, in addition to an initial electrical stimulation to induce muscle contraction, a plurality of further electrical stimulation pulses with intervals between each of said further electrical stimulation pulses, so that said further electrical stimulation pulses maintain said muscle contraction over a period extending from said initial electrical stimulation substantially up to a time just before a next expected R-peak.

33 Claims, 12 Drawing Sheets

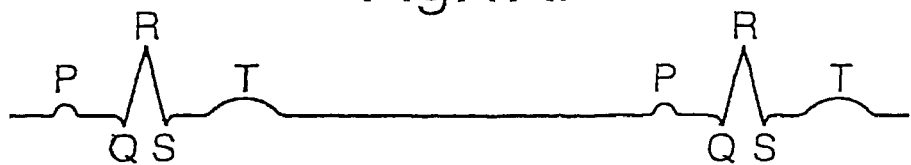
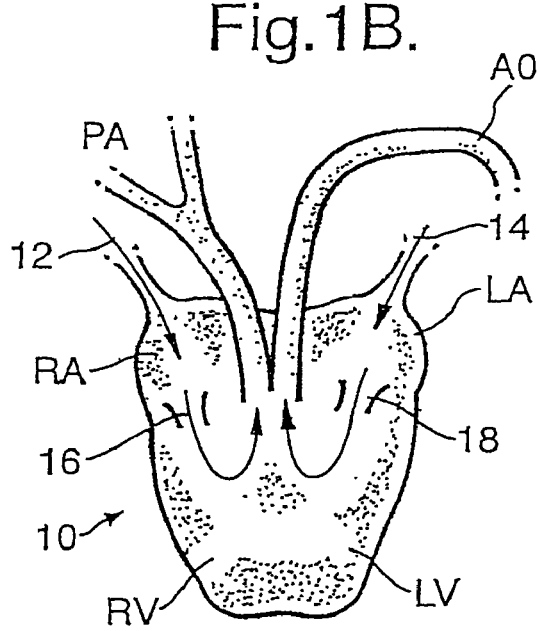
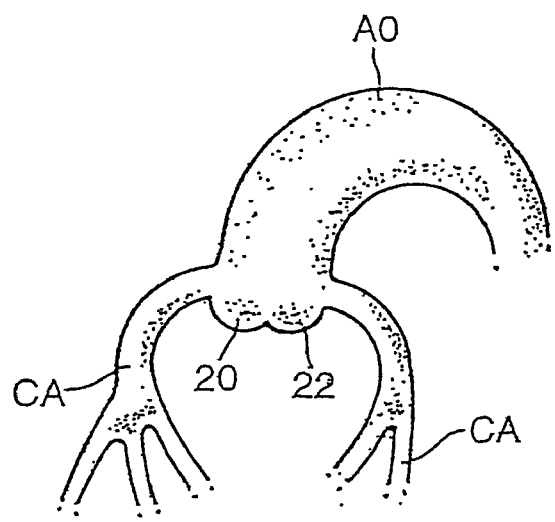

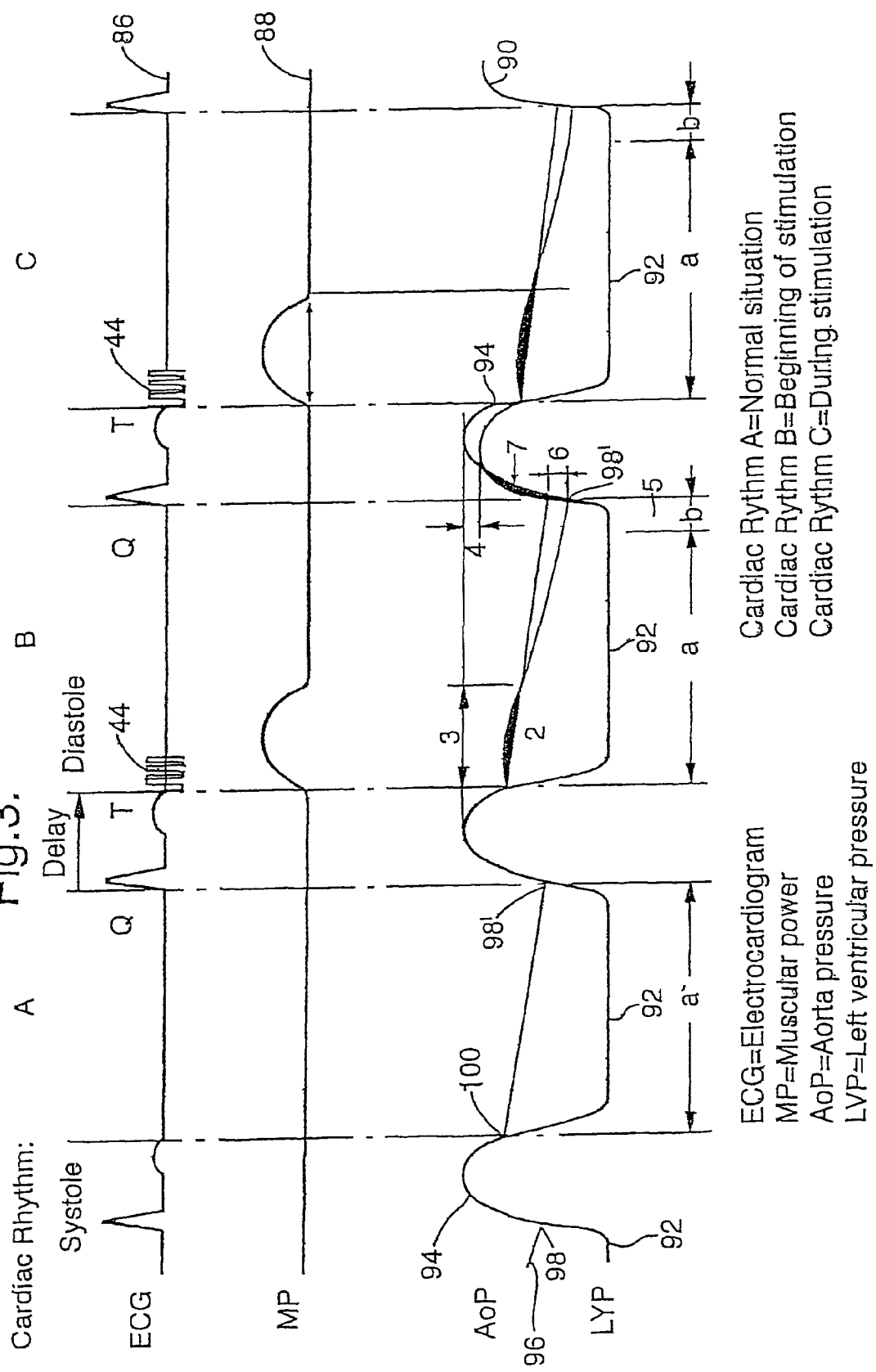

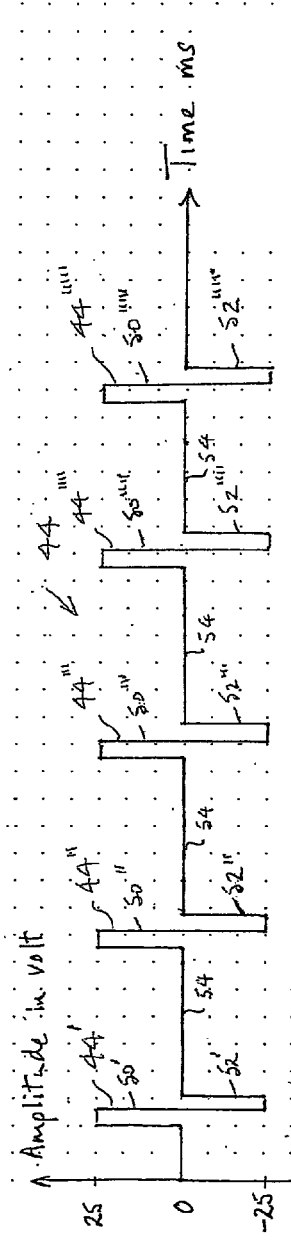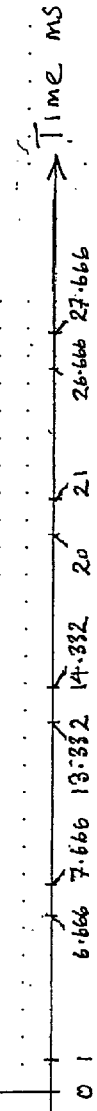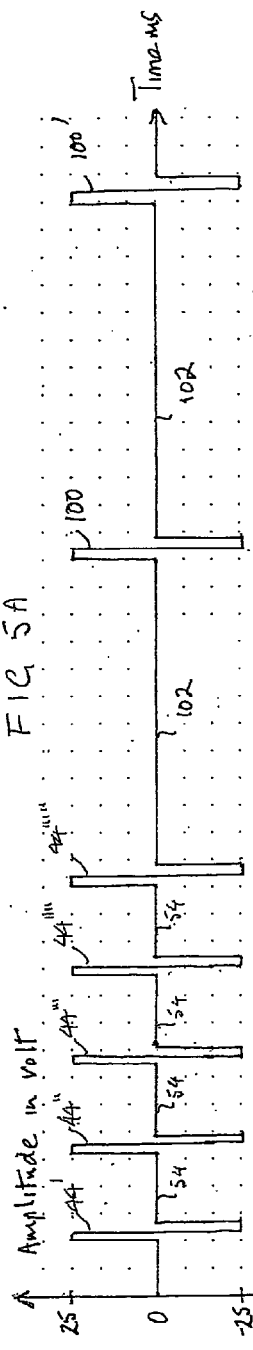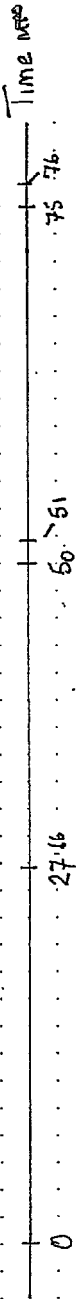
FIG 5A
FIG 5B

ELECTROTHERAPY APPARATUS AND METHOD OF TREATING A PERSON OR A MAMMAL USING SUCH ELECTROTHERAPY APPARATUS

CROSS-REFERENCES TO RELATED APPLICATIONS

This application is a continuation in part of U.S. patent application Ser. No. 10/994,981 filed Nov. 19, 2004, which is a divisional application of U.S. patent application Ser. No. 10/069,333 filed Jul. 15, 2002, which is the national phase of PCT/EP00/07933 filed Aug. 14, 2000, which is a continuation in part application of U.S. patent application Ser. No. 09/378,181 filed Aug. 20, 1999, and which further claims the priorities of PCT Application No. PCT/EP04/012619 filed Nov. 8, 2004, which claims the priority of European Patent Application No. 03025662.2 filed Nov. 7, 2003, the disclosures of all of which are incorporated herein by reference.

BACKGROUND OF THE INVENTION

The present invention relates to an electrotherapy apparatus comprising a sensor for detecting periodically recurring signal peaks, in particular the R-R peaks of an electrocardiogram of a person, a processor for deriving from the periodically recurring signal peaks a time delay corresponding to approximately the end of the T-wave, and a trigger system or circuit initiated by an output signal of the processor or embodied within the processor for applying a train of electrical stimulations to one or more active electrodes provided on the person at a time related to the end of the time delay. Furthermore the invention relates to methods of using such electrotherapy apparatus.

Electrotherapy apparatus of the initially named kind is described in the international patent application with the publication number WO 01/13990 A1.

The electrotherapy apparatus described there is adapted to stimulate the muscles of the body of a person or mammal using so-called counter-pulsation. That is to say, the momentary heart beat of the person or mammal is determined, generally by detecting the R peaks of an electrocardiogram derived in real time from the person or mammal being treated. From the distance in time measured between the last two R peaks a time is calculated corresponding to the end of the T-wave of the electrocardiogram using the known so-called Bazett relationship. The electro-stimulation pulses are then applied to the selected muscle generally starting within a window which extends from a time corresponding to 5% of the length of the R-R path before the predicted end of the T-wave after the last detected R peak up to a time corresponding to 45% of the length of the R-R path after the end of this T-wave. The prediction of the time at which the T-wave ends after the last detected R peak is based on the measured value for the R-R path length of the last heart cycle.

It has been found that this type of electrotherapy leads to extremely beneficial effects with respect to the heart of the person or mammal and, depending on precisely how the electrotherapy is carried out, can also be used for curing a whole spectrum of adverse conditions such as overweight.

In the aforementioned document WO 01/13990 the beneficial effect is primarily attributed to the specific shape of the curve in FIG. 3 of that reference showing a hump in the blood pressure curve just after the onset of diastole, which considerably increases the flow through the coronary arteries of the patient concerned, thus leading to an improvement of the condition of the heart muscles.

The experiments conducted to date seem to suggest that this explanation is only part of the story and that in fact even quite small local stimulations of a person or patient can lead to increased perfusion in the small peripheral blood vessels resulting in a significantly lower back pressure on the heart which itself improves the working of the heart. It is believed that some form of bio-feedback is taking place via the autonomous nervous system and that this accounts for the astonishing results that have been achieved.

The aforementioned document WO 01/13990 describes that, although the treatment can be carried out using just one neutral electrode and one active electrode, it is better if a plurality of active electrodes are used. The reason is that the human body becomes accustomed to the applied pulses and, if only one active electrode is provided, then the muscles affected by the electro-stimulation signals gradually become tired and are stimulated less effectively. By applying the stimulating pulses to different active electrodes in sequence it is possible to ensure that the muscle groups affected by the applied impulses do not become tired. It is stated that the minimum number of active electrodes for sequencing is two and a specific embodiment is described in which the train of stimulating pulses is applied in sequence to first, second, third and fourth electrodes.

The apparatus described in WO 01/13990 is provided with a safety cut-out function, meaning that the apparatus switches off automatically, if the patient's heart rate goes too high or too low, or if a patient's blood pressure becomes too high or too low or when arrhythmia is detected.

The prior art reference also describes a problem called interference.

This problem can be described as follows. When using any measured heart QRS trace (an electrocardiogram) a trigger signal for detecting the patient's heart rate is usually derived from the positive rising slope of every R peak. The trigger signal is generally a digital trigger signal and initiates the electrical muscle stimulation signal, after the required delay, at a time within the time delay window described earlier. Since this stimulation signal is an electrical signal with a magnitude many times higher than the heart rate signal itself, the electrical stimulation impulse is transmitted on the human body and consequently the heart signal sensor also senses the electrical stimulation signal. If now the control setting of the electrotherapy apparatus is such that a stimulation pulse for the muscle is delivered in counter-pulsation to the heart (i.e. at the end of the T-wave), the trigger unit first receives from the heart rate sensor the wanted trigger input representing an R peak. Moreover, during the R-R cycle, exactly at the moment of the muscle stimulation, a much higher electrical stimulation signal is delivered to the muscle which is interpreted as another R peak and results in a further trigger signal. This trigger signal then leads to a second unwanted muscle stimulation within the same R-R cycle at exactly the same delay but now after the further trigger signal. This second unwanted stimulation is perceived by the stimulated person as a sudden surprising disturbance which is completely irregular in comparison to the calming rhythm expected from the counter-pulsation mode. As a result the heart rate immediately increases sharply, probably via neuro-transmission to the brain and back to the heart. Synchronized stimulated counter-pulsation does not work when such interference is present and the wanted heart load reduction cannot then be achieved.

In order to overcome this problem the reference WO 01/13990 provides a gating mechanism which effectively closes an interference window after a trigger signal from a heart rate sensor has been registered by the electrotherapy apparatus. This interference window is reopened by the electrotherapy apparatus in time to accept the wanted trigger pulses but to avoid unwanted trigger pulses resulting from electro-stimulation.

The WO reference describes one practicable execution of the gating mechanism defining the interference window. This gating mechanism is realized in the form of software controlling a microprocessor whereby the rising edge of the digital trigger signal triggers the microprocessor into an interrupt routine and then the closing of the interference window is activated by a software gate which disables the acceptance of any unwanted trigger signal. Thus a further trigger signal resulting from electro-stimulation is prevented from being transmitted to the microprocessor as long as the interference window is closed. Closing and opening of the interference window is set by programmable adjustable setting values which are selected relative to the measured R-R cycle.

The WO reference also describes a practicable programmable algorithm which defines the way an adaptive control unit in the electrotherapy apparatus can automatically find the lowest possible heart load. In accordance with the description giving in the WO reference first of all realistic minimum and maximum values for the delay are defined, i.e. for the delay from each R peak to the triggering of a stimulation signal. These limits are set relative to the prevailing heart rate as measured from successive R-R peaks. The minimum delay will usually be selected at or just before the start of the delay window, i.e. at or just before a time corresponding to 5% of the R-R path before the expected end of the T-wave, for example as calculated using the so-called Bazett relationship. As a safety precaution a maximum delay can also be selected which should not be later than 45% of the length of the R-R path after the end of the T-wave. The maximum delay could, however, be omitted.

An offset value is now defined and is added to the minimum delay and used to define the time at which stimulation signals start. A typical initial value for the offset could be 5 to 10% of the R-R paths. Stimulation is now commenced using this time delay, i.e. minimum delay plus offset, and the heart rate is monitored by measuring the distance between successive R-R peaks. If a reduction of the heart rate, i.e. a lengthening of the R-R path, occurs, then a reduction in the offset is effected by a predetermined amount, for example a fixed fraction of the original offset, and a check is again made as to whether the heart rate has reduced. If so the offset is again reduced and this process is continued until no further reduction in the heart rate is detected, or alternatively, until the minimum heart rate set in the safety cut-out has been reached or until the heart rate increases again.

A renewed increase in the heart rate indicates that the delay (minimum delay plus offset) is no longer at an optimum value.

If the heart rate increases then the offset should also be increased in an attempt to reduce the heart rate. Once the heart rate starts to increase again then this is an indication that the offset is now too large. This signifies that the optimum value of the offset has been found, namely the value of the offset which resulted in a minimum heart rate. The offset can now be returned to this optimum value. Once a suitable offset value has been determined it can be retained for future use.

SUMMARY OF THE INVENTION

An object of the present invention is to improve the performance of the previously described apparatus and method to provide a significant improvement in hemodynamics, i.e. the blood circulation in the body and through the heart, while enabling significant heart unloading and to reduce the electrical loading of the human body, or at least not to seriously increase it beyond the electrical loading involved in the previously described invention.

In order to satisfy this object there is provided an apparatus of the initially named kind which is characterized in that the processor is adapted to generate, for each R-R period of a heart rate, a first train of electrical stimulation pulses having a first pulse repetition frequency and a first interval between successive pulses to induce an initial muscle contraction, and a plurality of further electrical stimulation pulses or groups of electrical stimulation pulses, the further electrical stimulation pulses or groups of electrical stimulation pulses being generated at intervals longer than the first interval between the pulses of the first train of electrical stimulation pulses, so that the further electrical stimulation pulses or groups of electrical stimulation pulses maintain the muscle contraction with a reduced energy input, the apparatus being adapted to apply the further electrical stimulation pulses or groups of electrical stimulation pulses to the person over a period extending from the first train of electrical stimulation pulses up to a time just before a next expected R peak.

The present invention is thus based on the realization that the heart unloading and improved circulation through the body and the heart of a person can be improved by maintaining the muscle contraction initiated generally at the predicted end of the T-wave for a period extending from the initial electrical stimulation substantially up to a time just before a next expected R peak.

The first train of electrical stimulation pulses preferably comprises a plurality of biphasic signal pulses.

The reasoning behind this arrangement is that relatively less electrical energy is required to maintain a muscle contraction once it has been initiated so that the muscle contraction that is aimed at can be prolonged for the desired time by a relatively small electrical input.

Whereas the first train of electrical stimulation pulses generally comprises from two to 10 individual pulses having a first pulse repetition frequency in the range from 50 to 250 Hz, preferably in the range from 100 to 200 Hz and especially of 150 Hz, the further electrical stimulation pulses are typically generated at a pulse repetition frequency in the range from 20 to 80 Hz, preferably in the range from 30 to 50 Hz and especially of 40 Hz. Moreover, whereas the first train of electrical stimulation comprises a plurality of pulses, the further electrical stimulating pulses are preferably single biphasic pulses. This also minimizes the electric loading of the human or animal body.

However, it is also possible for the further electrical stimulating pulses to comprise two or more individual pulses, i.e. a train or group of two or more individual pulses with intervals between successive trains or groups. Equally, the two or more individual pulses can be separated by an interval or can follow each other directly. In both cases a reduction in electric loading still occurs because the initial stimulating pulses are not continued for the full time necessary to produce a long muscle contraction.

Although it is possible to provide a plurality of interference windows to avoid electrical stimulating pulses being recognized by the apparatus as R peaks, this is rather more difficult with the apparatus of the present invention because of the need to repeatedly shut and reopen the interference window for each further stimulating pulse.

Accordingly, the present invention has found a way of providing assistance here, namely to use a heart rate sensor which is a non-electric sensor and is thus unaffected by the electrical stimulation pulses.

When such a non-electric sensor is used there is no need to provide an interference window.

As is apparent from the foregoing, the invention operates on the basis of the assumption that the heart beat following the last detected R peak will have essentially the same time duration as the last heart beat, or at least an average duration of the last few heart beats. This is of course by no means certain, particularly in the case of patients suffering from arrhythmia. Accordingly, although the microprocessor may be set to apply the last one of the further stimulating pulses so that the muscle contraction ends at a time corresponding to 85 to 95% of the R-R path length of the preceding heart cycle, or of an average value of the R-R path lengths of preceding heart cycles, the next heart beat could in fact be detected before the last further electrical stimulating pulse has been transmitted. Generally speaking, in order to terminate the muscle contraction at a time corresponding to 85 to 95% of the R-R path length since the last R peak, it is necessary to apply the last electrical stimulating pulse in a time window from 80 to 90% of the R-R path length after the last detected R peak.

The arrangement is preferably such that the interval between the further electrical stimulation pulses is selected to be greater than a time delay associated with a signal being initiated at the non-electric sensor by a new R peak and the processing of this signal by the processor. This means that if an R peak is detected before the last intended further electrical stimulation pulses there is a good chance that the generation of the last electrical stimulation pulses can be stopped sufficiently early to prevent the muscle contraction continuing into the systolic phase of the next heart cycle, which should be avoided if possible.

The apparatus preferably has a plurality of output channels for applying electrical stimulations to a plurality of active electrodes provided on the person being treated.

The reason for this is as follows:

It has been found that if a muscle is subjected to contraction signals once every heart cycle, then it can become fatigued. On the other hand, the present invention is not critical with respect to the muscle to which the contraction is applied. Accordingly, it is preferable to provide a plurality of active electrodes, for example four active electrodes, which each affect a separate muscle of a group of muscles or a region of muscles on the human body. Each channel of the electrotherapy apparatus is connected to a respective one of the active electrodes. Thus, if four active electrodes are present, the first channel can be connected to the first electrode and can provide electrical stimulation for a first muscle, the second channel can be connected to a second electrode and provide electrical stimulation for a second muscle, the third channel can be connected to a third electrode and provide electrical stimulation for a third muscle, and the fourth channel can be connected to a fourth electrode and provide electrical stimulation for a fourth muscle. This means that each muscle is stimulated only once every four heart cycles and there is therefore a rest period of three heart cycles between each electrical stimulation of any particular muscle. This avoids fatigue of the muscles.

The electrotherapy apparatus of the present invention thus applies the same electrical stimulation to each output channel in turn, each electrical stimulation comprising the initial stimulating pulses and the further stimulating pulses. Channel 1 is activated after one complete heart cycle has been detected, channel 2 is activated once a subsequent heart cycle has been detected and so on. The timing of the electrical stimulation signals applied to each channel is based on the R-R path length of the preceding heart cycle or on an average R-R path length of a plurality of preceding heart cycles.

This technique as described above also makes it possible to use different electro-stimulation signals, i.e. different stimulation signal shapes and values in each channel, which can also be beneficial under some circumstances.

An electrotherapy apparatus is particularly preferred in which a plurality of channel groups is provided, with each channel group comprising a plurality of channels. Each channel group preferably has the same number of channels. For example two or three channel groups can be provided and each channel group can comprise four channels.

There are a variety of special ways in which such an apparatus can be operated.

It is for example possible to provide each channel and each channel group with the same time delay. If it is assumed that four active electrodes are provided for each channel group then each channel of each group can be connected to a respective one of the four electrodes associated with that group. The apparatus can then be operated in such a way that channel 1 of the first channel group first stimulates a muscle or muscle group associated with the first electrode, and channel 2 of the first channel group then applies a stimulation signal to the second electrode, the second electrode being associated with a different muscle or a group of muscles from the first electrode. Channel 3 of the first channel group then applies a third stimulation signal to the third electrode and this stimulates a yet further different muscle or muscle group. Then channel 4 of the first channel group applies a stimulation signal to the fourth electrode and stimulates another muscle or muscle group associated with that electrode. This has the benefit that each muscle is stimulated only once every four heart beats and therefore each muscle or muscle group has a relaxation period of three heart beats before it is stimulated again. The reason for the value 3 is that the muscle is stimulated during each four heart beats for a period approximating to a heart beat. At the same time as each channel of the first channel group is applying stimulation to a muscle of a first group of muscles the corresponding channel of the second channel group is applying stimulation to a muscle of a second group of muscles and so on.

Thus, channel 1 of the channel group A is in operation at the same time as channel 5 of channel group B and, if three channel groups A, B, C are provided, at the same time as channel 9 of the channel group C. Channel 2 of channel group A is in operation at the same time as channel 6 of the channel group B and, if provided, at the same time as channel 10 of channel group C. Similarly, channels 3, 7 and 11 of channel groups A, B and C will operate at the same time as will channels 4, 8 and 12 of the channel groups A, B and C. The electrical stimulation provided in channels 1, 5 and 9 starts at the same time in each channel because the timing in these channels is based on the same preceding R-R path length. The electrical stimulation in channels 2, 6 and 10 also starts at the same time in each of these channels but can have a different delay in milliseconds after the last R peak because the timing for these channels is based on the next R-R path length and this may differ from the preceding R-R path length on which the timing of the stimulation in the channels 1, 5 and 9 is based. The same consideration applies to the timing of the electrical stimulation pulses in channels 3, 7 and 11 and to the timing of the electrical stimulation pulses in channels 4, 8 and 12.

Thus the muscles are stimulated in phase from the associated group of channels. Again, by using four channels for each muscle or group of muscles, a rest period of effectively three heart beats can be provided for each group of muscles.

Since there is a plurality of channel groups and since each channel group is used to stimulate different muscle groups on the body, the total stimulation can be enhanced in this way.

In another way of using an apparatus of the above-described kind, each channel group of output channels is associated with a respective muscle or group of muscles in general proximity to one another in a body of a person or mammal, the group of muscles associated with one group of output channels differs from the group of muscles associated with any other group of output channels and the stimulation signals transmitted from each group of output channels to the respectively associated group of muscles are triggered at different times for each group of channels.

More specifically, the group of muscles respectively associated with each group of channels can be disposed on a body of the person or mammal such that a group of muscles closer to the heart and associated with one group of channels is stimulated later than a group of muscles disposed further from the heart and associated with another group of channels. This has the effect that blood can be pumped by the muscle contraction from the periphery towards the heart.

Alternatively, the group of muscles respectively associated with each group of the channels can be disposed on a body of a person or mammal such that a group of muscles further from the heart and associated with one group of the channels is stimulated later than a group of muscles disposed closer to the heart and associated with another group of channels. This helps to pump blood from the heart to the periphery of the body and can be of benefit in increasing the blood flow through a particular part of the body, for improving the blood flow to that part of the body, for example for recovery after an injury, and can also be used to benefit lymph transport in the body.

The present invention also relates to a method of treating a person or a mammal, the method comprising the steps of:
determining from the signal peaks of an electrocardiogram for at least a majority of the detected heart cycles a time corresponding to the distance between successive pairs of R-R peaks,
generating an initial electrical stimulation signal,
applying the initial electrical stimulation signal to a muscle or group of muscles of the person or mammal at a time related to the predicted end of the T-wave and lying in the range from −5% of the R-R path length of the preceding heart cycle, or of an average preceding R-R path length, before the predicted end of the T-wave, up to +45% of the R-R path length of the preceding heart cycle, or of an average preceding R-R path length, after the end of the T-wave, whereby to generate a muscle contraction, characterized by the further step of applying further electrical stimulation pulses to the muscle or muscle group to maintain the contraction for a time after the last detected R peak corresponding to 85 to 95% of the R-R path length of the preceding heart cycle, or of an average preceding R-R path length.

The invention will now be described in more detail by way of example only with reference to the accompanying drawings in which FIGS. 1 to 4 are generally similar to FIGS. 1 to 4 of the above-mentioned document WO 01/13990, but with certain modifications in FIGS. 2a and 4, and in which the remaining Figures pertain specifically to embodiments of the present invention.

BRIEF DESCRIPTION OF THE DRAWINGS

FIG. 1A is a schematic diagram illustrating a typical electrocardiogram,

FIG. 1B is a schematic diagram of the human heart,

FIG. 1C is an enlarged view of the aorta at the junction with the heart and with the coronary arteries, FIG. 3 is a set of diagrams showing the effect of the method and apparatus of the invention on the operation of the heart of a patient, FIG. 5A is a diagram to explain the preferred train of initial electrical stimulation pulses generated by the processor, FIG. 5B is a diagram to explain the relationship between the train of initial electrical stimulation pulses and the further electrical stimulation pulses generated by the processor.

DESCRIPTION OF THE PREFERRED EMBODIMENTS

Turning now to FIGS. 1A, 1B and 1C, a brief description of the normal operation of the human heart will be given in order to facilitate an understanding of the present invention.

The heart 10 shown in FIG. 1B has four chambers, namely the right atrium RA, the right ventricle RV, the left ventricle LV, and the left atrium LA. Venous blood returning to the heart flows into the right atrium, then into the right ventricle and passes to the lungs via the pulmonary artery PA. In the lungs the blood picks up oxygen and returns to the left atrium LA, as indicated by the arrow 14. From there, the oxygenated blood passes into the left ventricle, and then into the aorta AO, where it starts on its journey through the so-called big circulation around the body. The circulation from the right ventricle to the lungs and then to the left atrium is called the minor circulation.

The operation of the heart is associated with electrical signals, which are shown on the electrocardiogram of FIG. 1A. The point P signifies the contraction of the two atriums RA and LA, which pushes blood into the respective ventricles RV and LV via the respective valves 16 and 18, which act as non-return valves. The section of the electrocardiogram starting with Q and ending with T is referred to as the systole and represents the ventricle contraction which serves to expel blood from the right ventricle into the pulmonary artery, and from the left ventricle into the aorta. During this contraction, the valves 16 and 18 are closed to prevent reverse flow into the right atrium and left atrium. The section TQ is referred to as the diastole, meaning the relaxation or expansion of the ventricles. The heart is supplied with oxygenated blood via the coronary arteries CA, which branch off from the aorta just upstream of the valves 20, 22, which close to prevent blood returning from the aorta to the left ventricle during the diastolic phase. Clearly the heart, itself a muscle, must be supplied with oxygenated blood to keep the muscles working. The heart is supplied with this oxygenated blood via the coronary arteries CA during diastole. At T the valves 20, 22 of the aorta AO are closed and at this time the blood pressure in the aorta causes blood to enter the coronary arteries CA. Accordingly, an increase of the pressure in the aorta AO during diastole favors the coronary arteries.

As will be seen from the following, one of the important results associated with the present invention is a small increase in pressure in the aorta during diastole and this has been found to have a profound effect on the operation of the heart muscle.

Figure 2A:
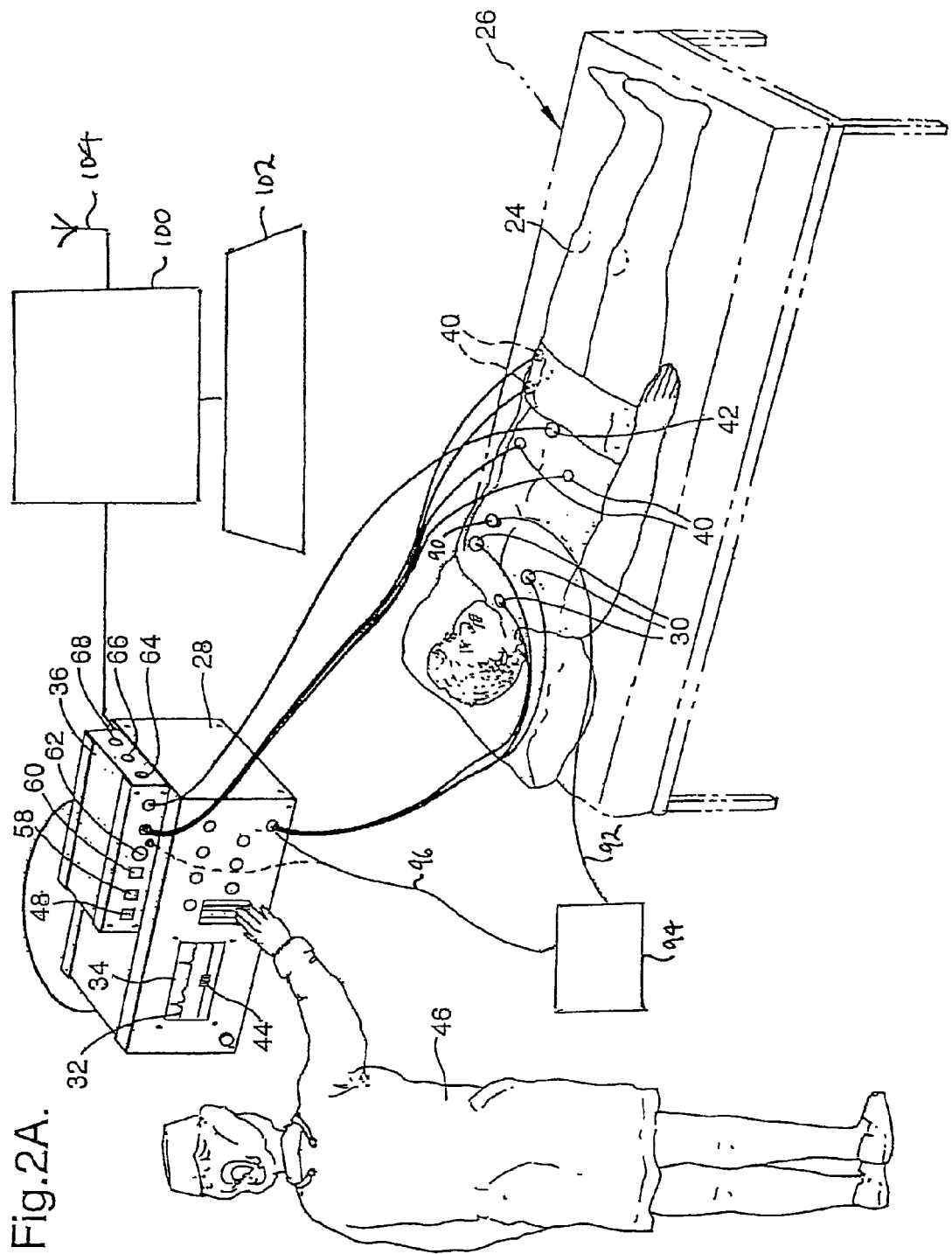
FIG. 2A is a schematic diagram of a first variant of an apparatus for applying electro-stimulation in accordance with the present invention.

FIG. 2A shows an illustration of a basic apparatus which has been used for the testing of the present invention and which clearly also represents a perfectly viable apparatus for practicing the invention, although a whole variety of further improvements and developments are possible, as will be described later.

As shown in FIG. 2A, a patient 24 is shown lying on a bed 26 and is connected to an electrocardioscope 28 via (in this embodiment) three sensing electrodes 30, which enable the electrocardioscope to show the ECG trace 32 for the particular patient 24 on the display 34. From the information available to the electrocardioscope through the three electrodes 30, a signal is extracted corresponding to the repetition frequency of the path R-R of the ECG trace of FIG. 1A. That is to say, this signal represents the frequency at which the patient's heart beats, i.e. his pulse rate.

Figure 4:
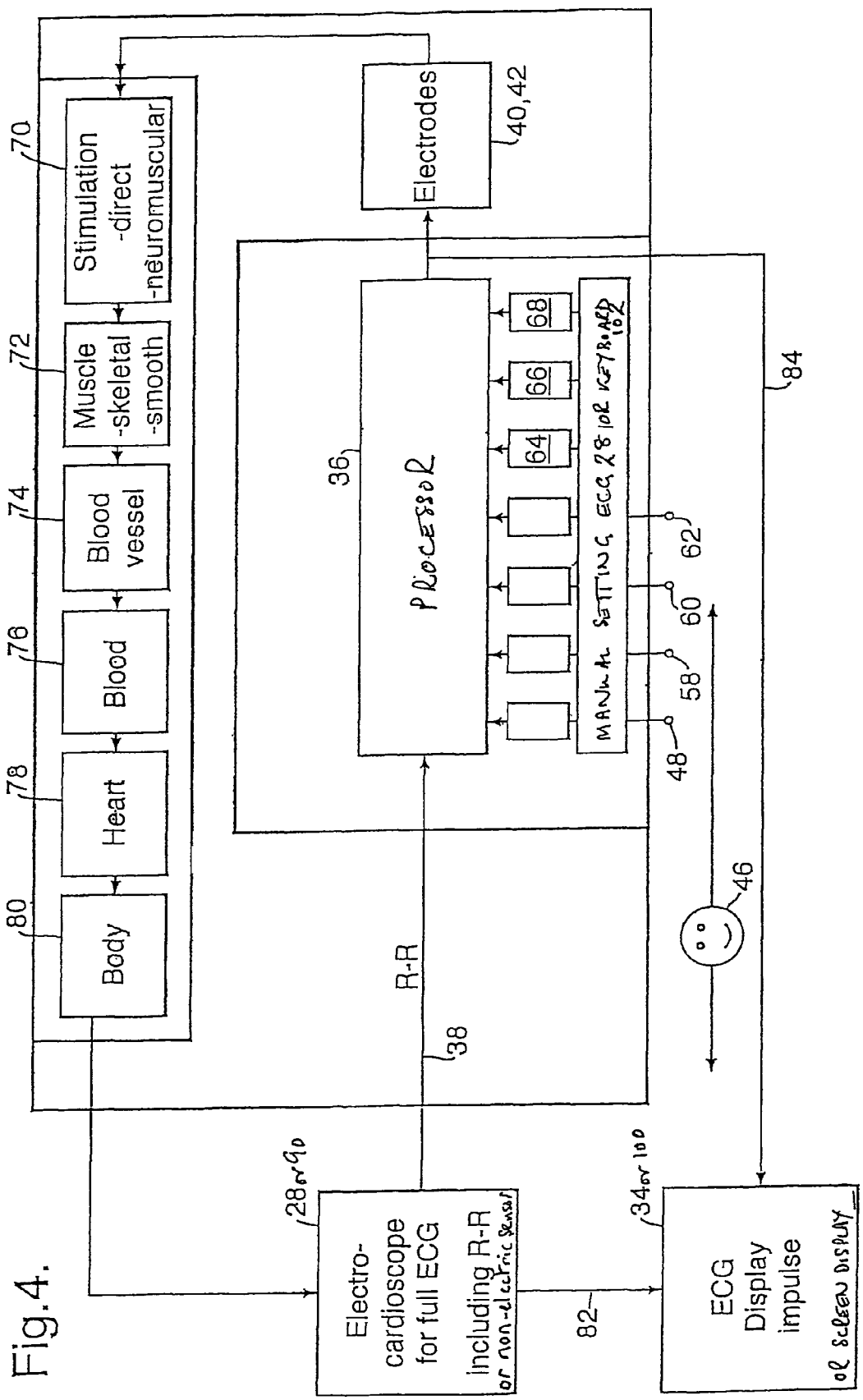
FIG. 4 is a schematic diagram illustrating the operation of an apparatus similar to that of FIG. 2A.

This signal is fed via a line 38, which is not shown in FIG. 2A but which is schematically illustrated in the diagram of FIG. 4 relating to the operation of the apparatus of FIG. 2A, to a processor 36 with an associated trigger system. In this embodiment the trigger system is embodied in the processor and suitable software is provided so that the trigger system delivers an initial electrical stimulation in the form of a train of biphasic rectangular pulses to the patient 24 via the active electrodes 40, of which four are shown in FIG. 2A. The precise shape of the train of biphasic rectangular pulses will be described later with reference to FIG. 2B. Although the trigger system is embodied in the processor in this example it could also be a separate unit (not shown) and simply receive trigger signals from the processor. In that case the output channels described here will not generally be present at the processor but at the output side of the separate unit.

The further electrode 42 is a neutral electrode necessary to complete the circuit. As illustrated in FIG. 2C the train of pulses 44 is triggered once per cycle of a patient's heart and is timed to coincide with the end of the T-wave of the electrocardiogram. The train of pulses 44 providing the initial electrical stimulation applied to the patient is also shown on the display 34 of the electrocardioscope, which enables the operator 46 to see the phase relationship between this train of pulses 44 and the electrocardiogram 34.

From the joint display on the screen 34 of the electrocardioscope of the ECG and the train of pulses 44 providing the initial electrical stimulation applied to the patient, the operator 46 can see whether the train of pulses has the appropriate delay relative to the Q-wave to secure the cardioresonance desired in accordance with the invention.

As noted earlier, the train of pulses is preferably set to start at the expected end of the T-wave. Depending on the circumstances it could, however, be set to start within a window extending from 5% of the R-R path length of the preceding heart cycle, or of an average preceding R-R path length, before the end of the expected end of the T-wave up to 45% of the R-R path length of the preceding heart cycle, or of an average preceding R-R path length, after the expected end of the T-wave. The operator 46 is able to adjust the phase for the start of each train of pulses, i.e. the delay, so that it coincides with, e.g., the end of the T-wave. This is one manual input into the processor indicated at 48 in FIGS. 2A and 4.

Before discussing the effect the train of pulses 44 applied to the patient has, it is appropriate to discuss the terminology used in this specification with respect to the pulses generated by the input system comprising the pulse generator 36 and the electrodes 40, 42.

Figure 2B:
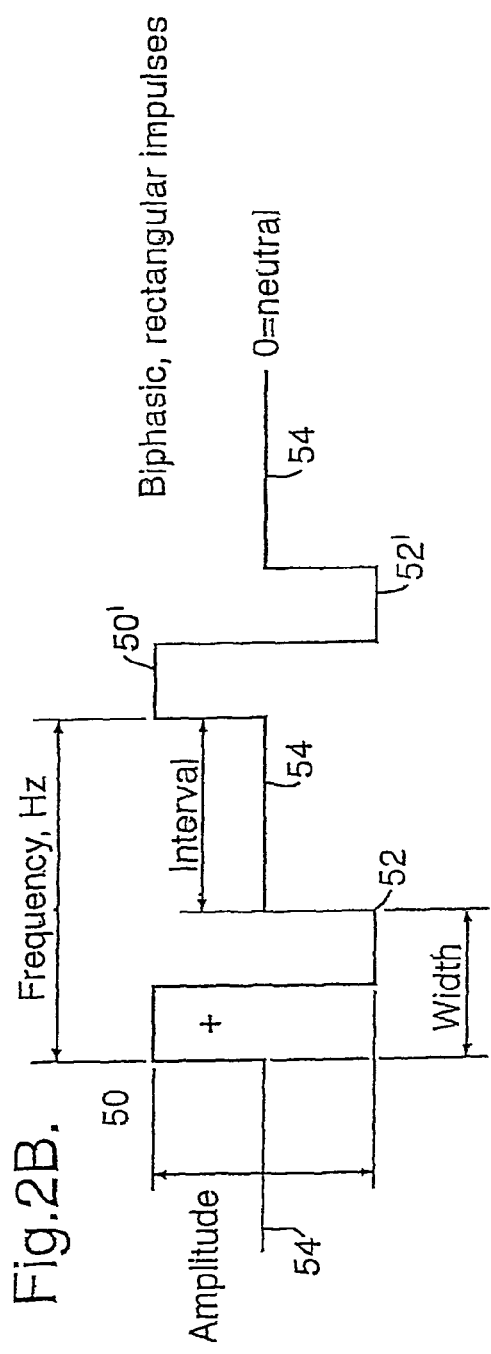
FIG. 2B is a graph illustrating the terminology used to describe a biphasic rectangular impulse.
Figure 2C:
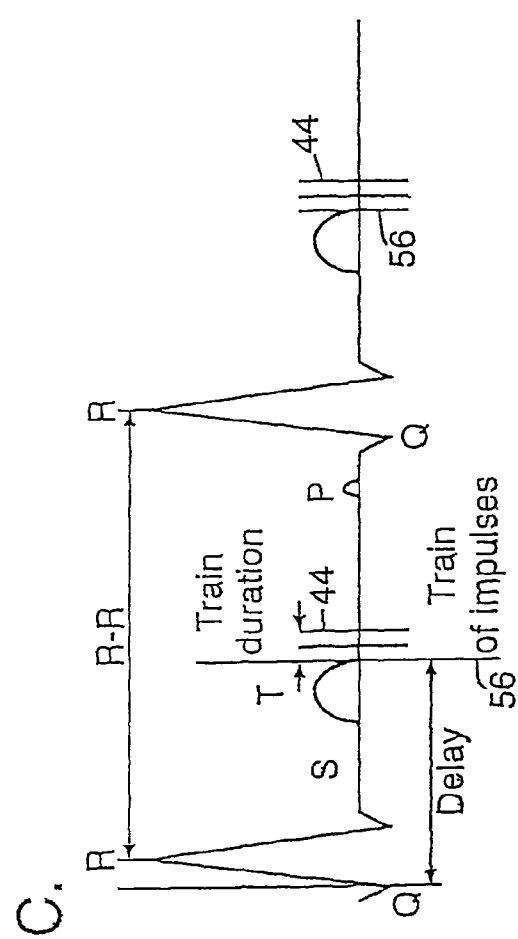
FIG. 2C is a graph illustrating the timing of the pulses applied to a patient in the counter-pulsation mode to achieve cardioresonance in accordance with the invention.

The basic output of the processor 36 is shown in FIG. 2B. It can be seen that the train of pulses providing the initial electrical stimulation comprises a plurality of so-called biphasic, rectangular impulses. Each biphasic rectangular impulse has a rectangular positive half pulse 50, and a rectangular negative half pulse 52 immediately following the positive half pulse, so that the impulse width is determined by the width of 50 plus the width of 52. The biphasic impulse 50, 52 of FIG. 2B is then followed by an interval and thereafter by a second biphasic impulse indicated as 50', 52' in FIG. 2B. The distance between sequential positive half waves 50, 50' of the biphasic pulses determines the pulse repetition frequency of the signal. During the interval between sequential biphasic pulses the voltage applied to the electrodes 40 is zero, i.e. is the same as the voltage at the neutral electrode 42, so that no stimulation of the patient occurs. This zero voltage is indicated by 54 in the diagram of FIG. 2B. It will be noted that instead of applying voltages to the electrodes, currents can be applied to them in which case the references above to voltages should be regarded as references to currents.

For the purpose of giving a reasonable example, the amplitude of the output signal of the pulse generator 36, i.e. as applied to the electrodes 40, can vary from a positive amplitude 50 of plus 40 V to a negative amplitude 52 of minus 40 V.

It must be stressed that these values are simply given by way of example and that substantial variations may be made, depending on a whole variety of factors.

So far as the amplitude of the biphasic signal is concerned, it has been found that different patients have different threshold voltages at which they perceive the treatment as being uncomfortable. Thus, one possibility is for the operator 46 to vary the amplitude of the biphasic pulses until the patient perceives them as being slightly uncomfortable and then to reduce the amplitude slightly so that the patient suffers no discomfort.

Generally speaking, an amplitude with a lower limit starting from slightly above zero volts (say, two or three volts) is possible. The upper limit depends on whether the patient feels comfortable with the voltage level applied and the resulting current (very high voltages could be used in theory at least, providing the current is restricted to non-damaging values).

The relationship between the pulse width and the pulse interval of each train of pulses determines the total energy input into the muscles stimulated via the electrodes 40, 42. While a ratio of about 1:5 has been found effective for the initial train of pulses 44 providing the initial electrical stimulation, this ratio can be varied substantially and indeed an interval is not absolutely essential. Generally speaking, with all patients a threshold is reached, depending on the pulse amplitude and the ratio of the pulse width to the interval, at which involuntary contractions of the muscle are apparent to a trained observer and the apparatus will usually be operated with amplitudes and ratios of the pulse width to pulse interval at levels at which apparent involuntary muscular contractions do occur, i.e. above the threshold value.

A particularly important reason for using biphasic pulses is to avoid the onset of electrolysis in the tissue affected by the applied impulses. Any effects of this kind which may be triggered during one half pulse are immediately reversed in the next half pulse. Although biphasic rectangular pulses of the kind described above have been found to be satisfactory and currently represent the preferred type of pulses, they are by no means the only possibility. Generally speaking, it is anticipated that the pulses delivered by the pulse generator will be biphasic in the sense that they have some positive going signal component and some negative going signal component. However, it is not out of the question that single phase rectangular pulses can also be used to advantage in some circumstances. It is certainly not essential that the negative half wave is of the same size and shape as the positive half wave. The positive half wave could be of different amplitude and width from the amplitude and width of the negative half wave. Moreover, it is not essential for the pulses to be rectangular pulses. They could be sinusoidal or they could have some other shape if desired.

As is apparent from FIG. 4, a preferred embodiment of the invention provides the operator 46 with various different parameters which he can set during the treatment of a patient. The first of these is the delay or impulse delay, which, as shown in FIG. 2C, is the time difference between the Q wave end of a QRS heart signal and the effective start of the impulses, i.e. the start of the train or burst of impulses which commences at the end of the T-wave. The operator 46 has the possibility of adjusting this delay at 48, for example, by varying a potentiometer which determines the delay as a percentage of the measured R-R path length, or by keying in a corresponding input to the processor, which is then put into effect by the programming of the processor. This is an extremely important adjustment in the apparatus of FIGS. 2A and 4 for the following reason:

As will be explained shortly, the effect of the pulses is to unload the heart. This manifests itself by a reduction of the pulse rate, i.e. of the frequency of the heart beat. This means that the time between successive R peaks of the ECG trace increases. Not only does R-R increase, but the distance from Q to the end of the T-wave also increases because it stands in a known relationship to the time interval R-R. Thus, if the delay were a fixed value, the start of the train of pulses 44 would not always coincide with the end of the T-wave due to the change in the pulse rate. Accordingly, when the operator sets the delay, this does not mean that he sets a specific value for the delay in milliseconds but rather that he specifies the delay as a specific percentage of the measured R-R path length.

The best results are frequently obtained when the delay is timed so that the first train of pulses is initiated at the end of the T-wave. However, beneficial results can also be obtained if the train of pulses starts slightly earlier or later than the end of the T-wave and, indeed, in some applications of the apparatus this is a desirable feature, as will become apparent from the later description.

Practically speaking, it is considered desirable to keep the start of the train of electrical stimulating pulses within a window extending from 5% of the length of the preceding R-R path before the end of the T-wave of an electrocardiogram up to 45% of the length of the preceding R-R path after the end of the T-wave. Instead of using the preceding R-R path, an average value of the R-R path over a plurality of preceding heart cycles can be used.

Another parameter which can be varied by the operator 46 is the duration of the train of pulses applied to the patient after the end of each T-wave. As shown in FIG. 2C, the duration of a train is defined as the time between the start and the end of the impulses within a train or burst of impulses. This possibility of variation is indicated in FIG. 4 by the reference numeral 58.

The complete train is the package of electric impulses which are repeated one after the other for the time defined by the duration of the train. The number of electric impulses in each train can be varied by varying the output frequency of the biphasic pulses, i.e. the pulse repetition frequency of the biphasic pulses in each train of pulses, i.e. the number of pulses that are repeated per second if the train of pulses were to be one second long. Furthermore, the duration of the train determines how long the stimulation with a given frequency is repeated, i.e. how many impulses are effectively delivered within one heart cycle. This pulse repetition frequency and in particular how it changes during each heart cycle can be varied by the operator 46 at the input 60 in the example of FIG. 2A and FIG. 4. This will be explained later with reference to FIGS. 5A and 5B. The other variable which can be readily changed by the operator 46 in the embodiment of FIGS. 2A and 4 is the amplitude of the biphasic rectangular impulses, i.e. the maximum difference between the peak value of the positive half cycle 50 and the peak value of the negative half cycle 52, as shown in FIG. 2B. This possibility of adjustment is indicated at 62 in FIG. 4. The amplitude is normally measured as a potential difference in volts. In an alternative embodiment (not shown) it is possible to plot a current curve rather than a voltage curve and to vary the amplitude with reference to the corresponding peak amplitude of the current curve.

In the apparatus of FIGS. 2A and 4 there are three further parameters of the pulses which are fixed, i.e. cannot in this embodiment be varied by the operator 46. The first of these parameters is the pulse width, i.e. the time before the start and end of an electric impulse, as shown in FIG. 2B. The pulse width is selected in the example of FIGS. 2A and 4, so that the interval at a pulse repetition frequency of 150 Hz is 5.66 times as long as the pulse width. That is to say, by fixing the pulse width the interval will automatically vary as the pulse repetition frequency is varied. If the pulse width is made variable, as it is in some other embodiments, then varying the pulse width automatically results in the interval shown in FIG. 2B varying, on the assumption that the repetition frequency of the pulses of the train of pulses does not change. Box 64 in FIG. 4 relates to the input at which the fixed value of the pulse width is selected.

The further boxes 66, 68 in FIG. 4 represent two further parameters of the output of the pulse generator, which in the apparatus of FIG. 2A and FIG. 4 are fixed and not readily variable by the operator 46. Box 66 relates to the impulse form, i.e. the geometric form of the electric impulse resulting when the amplitude of the electric impulse is displayed over the entire impulse width. In the present example this is a biphasic rectangular pulse but it could have different shapes, for example sinusoidal or saw-toothed.

Box 68 refers to the possibility of changing the impulse mode which relates to the alternating mode of how impulse forms are repeated between electric positive and electric negative phases of impulses. In the present example the impulse mode is clearly biphasic, with positive and negative, but otherwise identical electric impulses alternating one after the other. This mode switch would, however, allow the operator to select some other mode, for example two positive half pulses followed by one negative half pulse.

One other aspect of the invention should also be mentioned with reference to FIG. 2A. This is the possibility of using a plurality of electrodes 40, 42. As mentioned above, the electrode 42 is a neutral electrode and it is only necessary to provide one such neutral electrode. However, more than one neutral electrode can be used when different areas of the body are treated, in order to allow a neutral electrode to be in the vicinity of each active electrode or each group of active electrodes. For long-term treatment of a patient, it is recommended to provide a plurality of active electrodes 40.

The reason is that the human body can become accustomed to the applied pulses and if only one active electrode 40 is provided, i.e. only one electrode to which the biphasic rectangular impulse signal of FIG. 2B is applied, the muscles that are stimulated by the potential between this electrode and the neutral electrode 42 gradually become tired and are stimulated less effectively. By applying the stimulating impulses to the different active electrodes 40 in sequence, it is possible to ensure that the muscles of the muscle group affected by the applied impulses do not become tired. The minimum number of active electrodes for sequencing is two.

Experiments have shown that by applying the output signal of a pulse generator to several electrodes 40 in sequence the treatment can be carried out over a period of many days without problem, and indeed only two electrodes are sufficient for this. However, four electrodes are preferred.

In the experiments done to date the first train of pulses 44 has been applied to the first electrode 40 during one heart cycle, the next train of pulses 44 has been applied to the second electrode during a next heart cycle, the next train to the third electrode during a subsequent heart cycle, the next train to the fourth electrode during a further subsequent heart cycle and the next train to the first electrode during a later heart cycle and so on. However, a sequence of this kind is not essential. It could be perfectly feasible to feed several trains of pulses to one electrode and then to change to the next electrode, etc. Random energization of the electrodes with successive pulse trains or groups of pulse trains would also be entirely feasible.

It should be emphasized that there is nothing critical in the placement of the individual electrodes 40 and 42. Although these are shown in the stomach region of the patient under treatment here, they could be virtually anywhere on the patient's body. It is a surprising aspect of the present invention that the stimulation of any part of the peripheral vascular system with even small amounts of excitation energy have been found to produce the beneficial effect of the invention.

A more detailed discussion of the types of electro-stimulation possible will be given later in the description.

It will be noted that FIG. 4 also shows with a series of boxes how the stimulation input to the patient from the pulse generator affects the body. Box 70 indicates that the stimulation can be direct stimulation or neuro-muscular stimulation, which is more usual.

Box 72 shows that the stimulation can be applied either to skeletal muscles or to smooth muscles. The effect of applying the stimulation to skeletal or smooth muscles is in both cases to produce a pressure pulsation in a local blood vessel of the peripheral vascular system indicated by the box 74. This local pressure fluctuation propagates via the blood, essentially an incompressible liquid indicated by box 76, to the heart indicated by box 78. Provided the pulses are timed correctly and applied in accordance with the teaching of the present invention, then they have been found to have a significant effect in reducing the heart load, which itself has an effect on the body of the patient indicated by box 80. This effect is picked up by the electrodes 30 of the electrocardioscope.

As noted earlier, a signal corresponding to the pulse rate, for example the R-R signal, is then passed on to the pulse generator and triggers the generation of the biphasic rectangular pulses of the individual pulse trains. The ECG wave form 82 is shown on the display 34 of the electrocardioscope as is the output signal of the pulse generator, as shown by the lines 82 and 84 in FIG. 4. The operator 46 has the ability to vary the impulse delay to ensure that each train of pulses starts at the end of the T-wave of the electrocardiogram or at the position deemed optimal in a particular case.

FIG. 3 gives a graphic representation of the effect of the treatment with the method and apparatus of the invention. The topmost curve 86 shows several peaks of an ECG wave form and is divided basically into three sections A, B and C. Section A shows a patient's cardiac rhythm in a normal situation, i.e. without stimulation. Section B shows the cardiac rhythm for the same patient at the start of stimulation and section C shows the cardiac rhythm during continued stimulation. This division into sections A, B, C also applies to the further curves 88 and 90. In curve 86 section B shows the first train of impulses 44 providing the initial electrical stimulation which starts after the end of the T-wave and lasts for about 15% of the T-Q path. This same wave form repeats in phase C and continues repeating until the stimulation is terminated. The effect of this stimulation is to produce a significant reduction in the patient's heart rate so that the length between successive R positions of the ECG lengthens in the course of time. It will be noted that the R-R pattern in section C is longer than in section A, by a length labeled "b" as shown in curve 90 in FIG. 3.

Curve 88 shows the modulation of the muscular power resulting from the trains of electrical impulses such as 44 providing the initial electrical stimulation. In phase A of line 88, there is no stimulation and accordingly the line is a straight line. The first stimulation occurs in the section B and results in a stimulation of a muscle which affects the peripheral vascular system. It will be noted that the muscle contraction 3 starts at the start of the train of pulses 44 and tends to reach its maximum contraction at the end of the train of pulses and then relaxes over a time period rather longer than the train duration. It will be noted that the initial train of pulses 44 contains a plurality of stimulating electrical impulses but results in a simple muscular contraction. This muscular contraction 3 produces a pressure pulsation in the patient's peripheral vascular system which propagates back to the patient's heart.

The result of this can be seen from the curve 90, which is in fact a composite curve showing the pressure in the aorta and the left ventricular pressure. The left ventricular pressure starts from a base line value 92 and increases smoothly into a rounded peak 94, which has a value above the base line value 92 from the start of the Q wave until just after the end of the T-wave. Superimposed on this curve is a curve 96 for the pressure in the aorta.

At the point 98 the valves 20, 22 in FIG. 1C open and the pressure in the left ventricle is communicated directly into the aorta so that the pressure in the aorta rises at the same rate and with the same value as the pressure in the left ventricle until the end of the T-wave is reached, i.e. until the point 100 in FIG. 3, where the valves 20, 22 close again and the pressure in the aorta gradually sinks as the blood in it moves through the arteries of the human body. At point 98' the valves 20, 22 open again and the cycle repeats.

The effect of the muscular contraction, indicated by 3 in the curve 88, is to modulate the pressure in the aorta by a pressure wave traveling back to the aorta, from the peripheral blood vessel pulsation induced by the muscle contraction, so that in phase B it is slightly higher—shown as a visible hump—in the region labeled 2 than the corresponding value in phase A of curve 96. However, after the end of the muscular contraction, the pressure in the aorta sinks to lower values than were present in the corresponding section of the pressure curve in phase A.

At the same time it will be noted that the peak 94" of the left ventricular pressure has also reduced relative to the peak value 94 in phase A. The reduction is labeled 4 in FIG. 3.

What this means in practice is that the hump 2 in the pressure in the aorta in diastole results in increased coronary circulation; i.e. more blood and more oxygen are being supplied to the heart muscles, resulting in more energy being made available to the heart. This causes the pulse rate to reduce so that the duration of each heart beat increases from the value a before stimulation by the amount b to the value a+b after prolonged stimulation. The typical measured reduction with various probates is about 10 pulses per minute in the rest mode, for example 70 down to 60, or up to 30 or more at a high pulse rate, for example from 140 to 110, because of an increase of the DPTI/TTI ratio (diastolic blood pressure time index/time tension index).

In addition, the reduction indicated by 4 from the peak value 94 in the phase A to the peak value 94" in the phase C represents a fall in the systolic pressure in the left ventricle and thus reducing left ventricular wall tension.

Bearing in mind that the heart load is proportional to the pulse rate times the systolic pressure, the effect of the invention in lowering both pulse rate and systolic pressure leads to a significant reduction in heart load.

The pre-systolic blood pressure, i.e. the pressure at the points 98, 98', 98" in FIG. 3, seems to reduce by about −5 mm Hg for a probate with normal blood pressure of 120/60. Extremely beneficial is the fact that with patients with blood pressure which is too high the reduction is far more pronounced, although the reduction in the heart rate for such patients tends to be less than for normal patients.

It is also noted that the cardioresonance electro-stimulation of the invention not only results in a lower systolic pressure but also a steeper pressure increase in the systole, which can also be seen from curve 90 in phase C of FIG. 3.

Generally speaking it can be said that DPTI increases by some +10% to 15% depending on probates resulting from the hump in the blood pressure increase in diastole, reduced heart pulse rate and corrected by the difference from reduced pre-systolic blood pressure, assuming probates with normal blood pressure.

TTI decreases by some 4 to 5%, resulting from lower pre-systolic blood pressure corrected by the steeper pressure increase in systole (as shown at 7 in FIG. 3).

The benefit of this is that the DPTI/TTI ratio consequently increases by some 15 to 20% depending on probates for those having normal blood pressure. Thus, the typical heart load reduction is some 10 to 25% or more depending on the probates and their physical condition, which results from lower heart pulse rate and reduced systolic blood pressure and lower pre-systolic pressure. Furthermore, myocardial contractivity is improved, coronary blood circulation increased and ischemia reduced.

Turning now to FIG. 2a there can be seen a further sensor 90 which is connected by a lead 92 to a sensor signal processor 94 which is in turn connected, for the purpose of illustration, via a lead 96 to the electrocardiograph 28. The sensor 90 is a heart signal sensor of a non-electrical kind. It can for example be an acoustic sensor which detects the heart signal by the different acoustic noises generated during the operation of the heart. The acoustic signals are converted by a transducer into electrical signals and are processed in the device 94 to generate a signal corresponding to the electrocardiogram 32 shown in the electrocardiograph 28.

Various different types of non-electrical sensors 90 are known and all can be used for the purposes of the present invention. For example the non-electrical sensor can be selected from the group comprising a non-invasive, aortic pressure measurement device, an invasive aortic pressure measurement device and a noise detection device adapted to detect the closing of the heart valves. The benefit of using a non-electrical sensor is that the sensor is not disturbed by the electrical noise resulting from the electrical stimulation of the muscles. In fact, when such a sensor is used, the electrocardiograph 28 is actually redundant and therefore the lead 96 could lead, as is shown in dotted lines by the reference numeral 98, directly to the signal processor 36. Generally speaking the processor 36, which can be a PC, will be connected to a screen 100 with a keyboard 102 and the operator or physician 46 can then observe the heart trace on the screen (if desired) and can input parameters for the operation of the processor into the computer 36 via the keyboard. In addition reference numeral 104 signifies an internet connection which enables the physician or operator 46 to download new or updated operating programs for his electrotherapy apparatus which are made available as so-called firmware by the manufacturer of the electrotherapy apparatus.

A brief description will now be given as to how the processor 36 basically operates to provide electrical stimulation signals.

The processor either receives signals from the electrocardiograph 28 or from the non-electrical sensor 90 (or from both) and is programmed to recognize the R-R peaks of the electrocardiogram, these being the largest signal peaks and being the easiest to recognize. The processor first makes a determination for each successive pair of signal peaks of a value corresponding to the time between the successive pairs of signal peaks and thus to the person's heart rate. For example, if the patient has a regular heart beat of 60 beats per minute, then the time between successive pairs of R-R peaks is one second or 1000 milliseconds. Generally speaking a person's heart rate is not entirely regular and with many patients in need of treatment for heart problems it is definitely irregular. This means that the distance between successive pairs of signal peaks fluctuates and may vary significantly from the 1000 milliseconds of the example given above.

The electrotherapy apparatus of the present invention is designed to deal with hearts beats as low as 30 per minute and as high as 250 per minute. Outside of these limits, which are given by way of example only, the electrotherapy apparatus cannot operate and thus, for each successive pair of signal peaks detected, a determination is made of whether the distance between the R-R peaks lies within the range in which the apparatus is physically capable of operating. For example 30 beats per minute corresponds to a time between R-R peaks of 2000 milliseconds, and a heart beat of 250 corresponds to a period of 240 milliseconds. Generally speaking heart rates of 30 and 250 are extreme and the electrotherapy apparatus preferably has an input, which can be made via the keyboard 102, enabling the operator to set the limits to a narrower range, for example 40 to 170 beats per minute.

The processor 38 is programmed to compare the measured time between each pair of R-R peaks with the range of values technically permitted by the apparatus and/or with the maximum and minimum permissible operator-selected limits. Clearly the operator-selected limits must be narrower then the technical limits, and, if these limits are input by the operator, then it is sufficient simply to make the comparison with these limits. On the other hand, if no limits are selected by the operator, it is only necessary to carry out the comparison with the maximum and minimum permissible technical limits.

The operation of the apparatus basically relies on the heart rate not fluctuating wildly and is specially adapted to cope with the problems that arise if the patient is suffering from irregular heart beat, arrhythmia.

In this connection the processor 36 is first programmed to determine whether the time between successive R-R peaks exceeds a preceding value, i.e. the distance in time between the R-R peaks of the preceding heart beat, or a preceding value averaged over a plurality of heart beats, by more than a defined amount. In addition the processor is programmed to determine whether each measured R-R value is less than a preceding value, again typically the R-R value for the preceding heart beat, or less than a preceding value averaged over a plurality of heart beats, by more than a defined amount.

The processor is programmed, so that it only triggers the generation of an electrical stimulation pulse when the comparison with the maximum and minimum technical limits and/or the maximum and minimum permissible selected limits is favorable and when the determinations referred to above show that the measured R-R value does not exceed the preceding R-R value, or the preceding average R-R value, by more than a defined amount and is not less than the preceding value, or the preceding average value, by more than a defined amount.

If the comparisons are unfavorable or the determinations are unfavorable, then no trigger pulse is generated and the apparatus simply continues measuring the distance between successive pairs of R-R peaks until a plurality of successive values are found which satisfy the above criteria.

Once the R-R value is known for a particular heart cycle the processor is also able to calculate, using the known Bazett relationship, the number of milliseconds till the expected end of the T-wave for the next heart beat. Rather than calculating this value using the Bazett relationship the processor can also be programmed to look up the corresponding value in a suitable look-up table or other statistical database.

Should the operator or physician decide that the stimulation will not be carried out precisely at the end of the T-wave, but at a slightly earlier or later time, then he can input the required offset value (as a percentage, e.g. by varying the proportionality constant in the Bazett relationship) into the keyboard and it will be adopted by the system.

In addition to calculating the time delay to the end of the T-wave the processor is also programmed to calculate a maximum stimulation length which is intended to ensure that stimulation ends at a time sufficient to ensure that one muscular contraction has terminated before the next expected R peak arrives.

Furthermore, the processor is programmed to check that the calculated or derived value of the time delay is greater than or equal to a delay time equivalent to a trigger delay plus a calculated delay. The trigger delay is the delay between initiation of a trigger signal delivered by the sensor corresponding to the detection of a first signal peak and the time this signal reaches the processor, and the calculation delay is the time required by the processor to calculate the delay. If the calculated delay time to the end of the T-wave is shorter than a delay time equal to the trigger delay plus the calculated delay then the processor is programmed to arbitrarily set the calculated time delay to an adapted value greater than or equal to the delay time equivalent to the trigger delay plus the calculated delay.

In addition the processor is programmed to check that the calculated time delay, or the adapted time delay, is less than or equal to the maximum stimulation length and to revise it if necessary so that it is less than the maximum stimulation length.

The processor is also programmed to calculate a duration of the electrical stimulation based on the input parameters and a maximum duration equal to the maximum stimulation length minus the calculated time delay or the adapted time delay and to check whether the calculated duration is less than or equal to the maximum duration. If it is not, then the duration has to be adapted so that it is less than or equal to the maximum duration.

This process is repeated for each completed heart cycle.

If a further signal peak is not detected within an expected time calculated by the processor and based on a preceding value, or a preceding average value, then no trigger signal is transmitted and the transmission of the trigger signal and thus stimulation is inhibited until further signal peaks are detected within the expected limits.

Instead of using a value of the preceding time between signal peaks as a value for the R-R path it is also possible to use an average value formed from a plurality of past values. In this way it is possible for the processor to be programmed to include in the plurality of past values those values which lie within a range less than the preceding measured value plus a predefined positive deviation and more than a value corresponding to the preceding measured value less a predefined deviation. This means that only reasonable values are taking into account in forming the average value and thus increases the reliability of the system.

The purpose of using such an average value is to improve the quality of stimulation and avoid wrong settings in the case of arrhythmia. It is known that the systole length remains more or less regular in the case of arrhythmia whereas the length of diastole can vary greatly leading to large heart rate fluctuations. In such a case it has proved successful to continue stimulation with an average history being used for calculating the delay and with stimulation occurring despite the fact that the current measured heart rate is outside of the heart rate deviation criteria that have been set. In such a case the heart rate would not be considered during the calculation of the sliding average but the stimulation is continued with the historical average for calculating a relatively correct delay to be used to stimulate after the end of systole. However, as stated above, diastole varies heavily with such a system.

If the sliding average is used then a definition must be given as to how many regular heart beats satisfying the criteria of heart rate deviation, i.e. lying within the positive and negative limits described above, can be used as a basis for determining whether, following arrhythmia, "good" recorded heart beats are included again into the sliding average to adapt to the newly prevailing situation. It has been found that a reasonable result can be obtained if three regular heart beats are detected following arrhythmia and can be included in the sliding average to adapt it to the newly prevailing situation.

Basically the determination of the heart rate, the distance between two R-R peaks, could be performed from any past number of heart rates from N=1 or N>1 and any heart rate which fails the deviation test (lies outside of the maximum and minimum limits based on this average value) will not be considered for forming the sliding average until at least one regular heart beat or a plurality of regular heart beats (typically three heart beats) have been detected again. A regular heart beat means a heart beat which lies within the positive and negative limits set relative to the average heart rate.

Turning now to FIGS. 5A and 5B an explanation will be given of the preferred form of the electrical stimulation applied to a person or patient during each heart cycle.

FIG. 5A shows the first train of pulses 44 comprising the individual biphasic pulses 44', 44", 44''', 44'''' and 44''''' providing the initial stimulation. Each pulse of the train of pulses providing the initial electrical stimulation is a biphasic pulse having the same general form as shown in FIG. 2E. The frequency, i.e. the pulse repetition frequency of the pulses 44 providing the initial electrical stimulation, is selected in this example to be 150 Hz. This means that each pulse has a duration of 1000 ms divided by 150=6.66 ms. The width of one biphasic pulse, i.e. of one positive half wave and one negative half wave immediately following the positive half wave, is 1 ms. Thus, if the time is started at the rising flank of the first biphasic pulse shown at the left-hand side of the diagram of FIG. 5A, then the value of 0 ms can be written beside it, as shown on the timescale beneath the start of the train of pulses 44 in FIG. 5A. Thus, the first biphasic pulse has terminated after 1 ms and the next starts at 6.666 ms so that there is an interval of 5.666 ms between the end of the first pulse 44' in FIG. 5A and the beginning of the next pulse 44" in FIG. 5A. The times at which the subsequent pulses 44''', 44'''', 44''''' and 44'''''' start and finish are all entered on the timescale of FIG. 5A.

As can be seen from FIG. 5B the train of pulses 44 comprising the five individual pulses 44', 44", 44''', 44'''', 44''''' providing the initial electrical stimulation and generating the muscle contraction is followed by further stimulating electrical pulses 100, 100', etc. with a longer interval 102 between the individual pulses so that these are triggered at intervals 102 of 25 milliseconds corresponding to a pulse repetition frequency of 40 Hz. These further stimulating electrical pulses are intended to extend the muscle contraction up to a time shortly before the next R peak.

Thus, the main purpose of the present invention is to control and extend the end of contraction of the muscles subjected to electrical stimulation thus improving hemodynamics by some 20% while reducing electric loading of the human body.

The way this is achieved will be explained further with reference to FIGS. 6 and 7.

Figure 6:
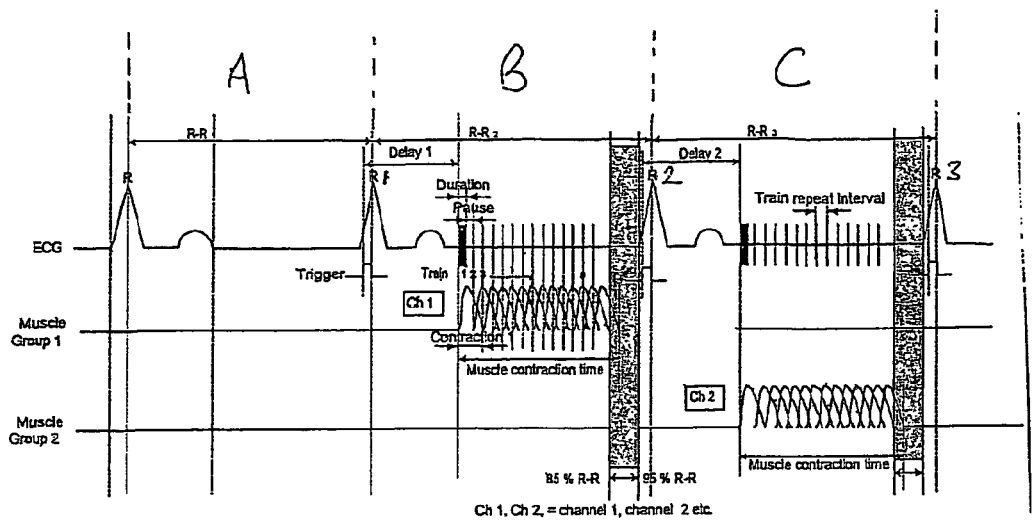
FIG. 6 is a diagram explaining how the electrical stimulation pulses are timed in an attempt to ensure that the muscle contraction is concluded before the next R peak.

FIG. 6 shows a diagram similar to the graph of FIG. 3 but also illustrating the muscle contraction achieved. Again, FIG. 6 is divided into three sections A, B and C, with section A representing the case of no electrical stimulation, section B representing the start of the electrical stimulation and section C the situation with continued electrical stimulation.

First a delay (Delay 1) to fit into the window (−5% to +45% of R-R measured from end of T-wave) is calculated based on the last measured R-R path length, or on an average value for the preceding R-R path length. A first short train of impulses (Train 1=44 in FIGS. 5A and 5B) is being delivered just sufficient to trigger a first short muscle contraction (Contraction 1). After a pause (defined by technical limits=1 or more than one impulse) a new set of multiple very short trains (Train 2, 3, . . . n) is delivered. In this example the "trains" 2, 3, . . . n are further electrical stimulating pulses in the form of single biphasic pulses as shown by the further electrical stimulation pulses 100 in FIG. 5B. Each "train" 2, 3, . . . n is just sufficient to maintain the muscle contraction, which is being perceived as one single muscle contraction. Based on experience, which results from measurements, the length of the first muscle contraction (Contraction 1) is calculated as having approximately three times the duration of train 1 and each subsequent very short train (Train 2, 3, . . . n) of impulses triggers an additional muscle contraction wave, which is being superimposed on "Contraction 1". Again the additional increment of the muscle contraction in time can be calculated, because it is known that the descending slopes of "Contractions 2, 3, . . . n" are creating a extension of the "Contraction 1" (=parallel shifting of "Contraction 1" on the time axis). By this method the total muscle contraction time resulting from "Trains 1 plus 2, 3, . . . n" can be calculated by the microprocessor to have the last extension of "Train n" and "Contraction n" to end within a window of 85-95% of the last (or average of more than one last) R-R1 (the last one available at the time of calculation which takes place after the detection of R-R1).

Thus, using the typical example of FIGS. 5A and 5B: Train 1: Frequency 150 Hz, Duration=3% of R-R (allowing five impulses of 6.666 ms at impulse width of 1 ms length and at e.g. 60 bpm heart rate, giving a duration=30 ms), amplitude of e.g. 25 V, pause=three impulses of train 1=20 ms. This train 1 will trigger a muscle contraction of typically 90 ms "Contraction 1". Train 2 consequently will start after the elapsed time "Duration" of train 1, plus pause=50 ms after the beginning of train 1 and consist of only one impulse at same amplitude, train 3 is identical to train 2 and follows with a delay equal to the train repeat interval, i.e. every 25 ms a single impulse until n. In this example the trains 2, 3, . . . n are always identical single impulses every 25 ms, which could be considered as a single second train of impulses from train 2-n with a frequency of 40 Hz.

However this is only an example. The first train of pulses 44 could have fewer impulses than in the above example, the minimum (one or more than one) impulses to trigger a first muscle contraction, the shape of the amplitudes within the train could have any form, the pause could have a duration corresponding to more or fewer impulses or could have a fixed time in ms, as long as a following train 2 would be able to maintain the Contraction 1 and add an increment of muscle contraction time. Moreover, the trains 2, 3, . . . n could have a wider or more narrow time interval than the 24 milliseconds associated with the above 25 ms pulse repeat time (with a pulse width of one millisecond), again to allow to maintain the incremental contraction 2 and add another increment of muscle contraction time. The trains 2, 3, . . . n could have one or more impulses, with any shape of amplitude within each train, and furthermore the trains 2, 3, . . . n do not have to be identical. The trains 1, 2, 3, . . . n, could each also be referred to as groups of impulses or impulse groups.

The benefit of this technique is to minimize the electrical input (load) in to the human body and with this to avoid muscle fatigue and reduce adaptation of muscles to such a long stimulation, while achieving a muscle contraction time ending in a calculated window of 85-95% of R-R and giving at the same time an additional approximately 20% improvement in hemodynamics. The same muscle contraction time could be achieved by simply extending train 1 to last as long as required. In above example the train 1 would have to be repeated and would have to deliver its last impulse at the moment of impulse n. Since the electric input is the integral of the amplitude for the impulse width times the number of impulses during the train it becomes clear that, in above example, the electric input for the invention with the multiple trains is only slightly above 20% (actually the difference of electric input of train 1 to the average of the trains 2, 3, . . . n) to achieve the same muscle contraction time.

With regard to a faster end of the descending slope of the muscle contraction it is favorable to use the shortest possible train 1 resulting in the "master" contraction 1, which is then maintained by the following short impulses. In the above example, the contraction 1 lasts about three times the duration of train 1, with a descending slope of about 50 ms. This means that the muscle contraction n ends about 50 ms after the£ train n.

The shorter this descending train, the faster the muscle contraction increment can end.

It is now necessary to differentiate between two specific cases. In FIG. 6 the muscle contraction time is calculated by the microprocessor to end in the time window calculated with R-R1 to be within 85-95% of R-R1 after R1. The picture also shows the sequencing of the stimulation output signal from channel 1 to the electrode overlying a first muscle or muscle group 1, from channel 2 to an electrode overlying a second muscle or muscle group, etc. Providing the next R peak, i.e. R2, occurs after the end of the predicted window, i.e. after 95% of R-R1 after R1, all is well. However, R2 could occur before the end of the predicted window and therefore the muscle contraction could extend into the systolic phase of R-R3, which is undesirable. This situation is illustrated in FIG. 7.

Figure 7:
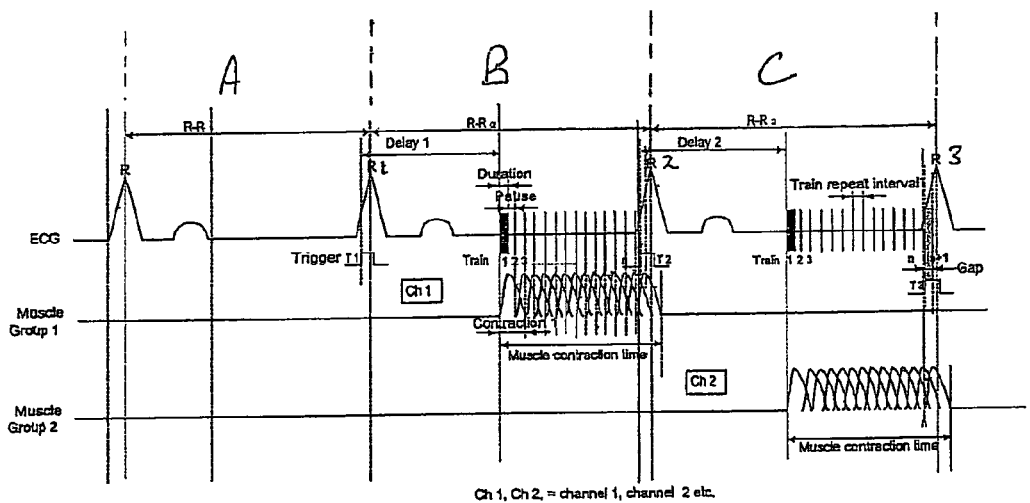
FIG. 7 is a further diagram explaining what happens when the next R peak arrives earlier than expected.

In FIG. 7 the muscle contraction time is extended (compared to FIG. 6) and is terminated with the last train n after the sensor has detected the following peak R2. The sensor has triggered trigger signal T2. At the first rising vertical slope of the trigger signal T2 the microprocessor of the device will end the continuation of adding additional trains (i.e. train n+1 is no longer transmitted). The muscle stimulation time consequently ends after the conclusion of the muscle contraction increment n added by train n has concluded the muscle contraction with the final descending slope.

It has to be noted that there is a technical time difference, called "Gap" in FIG. 7, which has to be observed. It represents the transmission delay time from the time the sensor detects the following R-wave (R2 in FIG. 7) to the time the first vertically rising slope of the trigger signal is processed by the microprocessor. A typical transmission delay is around 20 ms. FIG. 7 shows an example, where the train repeat interval, i.e. the time between train n and train n+1, is 25 ms. In this example, the vertical slope of the trigger signal T3 is being sent just shortly after the beginning of train n. The transmission delay of 20 ms is just smaller than the gap (time difference between the rising vertical slope of trigger T3 and the following train n+1) and in this example the microprocessor can just prevent train n+1. For cases in which the selected train repeat interval is smaller a smaller gap will result. Train n+1 can no longer be prevented by the microprocessor if the gap becomes smaller than the trigger signal transmission delay. For such cases, the microprocessor will prevent train n+2, meaning that the muscle contraction time will be extended by the train repeat interval.

Two cases need to be distinguished:
a) The case when an ECG signal is used for the determination of the R peaks.

Figure 8:
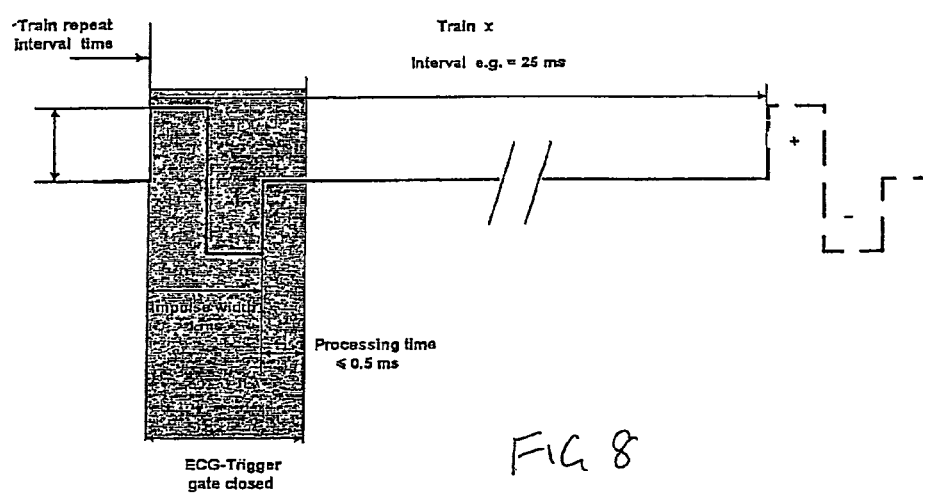
FIG. 8 is a diagram illustrating the concept of interference windows.

In this case, an electronic gate would have to be used to close the trigger signal input to the microprocessor exactly with the first impulse of each train and to reopen it immediately after the end of the last impulse width of each train. This is illustrated in FIG. 8 for a train x in FIG. 12 in order to eliminate the possibility of self-induced triggering by the electrical impulse delivered. In the above example with a 25 ms train repeat interval and a single impulse per train with an impulse width of 1 ms and an assumed gate opening speed (processing time) of less than 0.5 ms, the ECG trigger window would be open for more than 23.5 ms or more than 94% of the stimulation time in-between train 2, 3, . . . n. This is predictable but involves the risk that an R peak may be missed if it takes place at a time when the ECG trigger window is closed.
b) The case when a non-electrical sensor is used for the determination of the R peaks.

An additional, non-electrical sensor (e.g. triggering on the rising or falling slope of a non-invasive or invasive aortic pressure measurement, or triggering on the noise detection of the closing of the heart valve, etc.) would be used for application for which an intermittently closed ECG trigger gate is unacceptable or for any application. By non-electrical sensor is meant a sensor which does not detect voltages or currents related to the operation of the heart but, for example, relies on pressure or noise measurements to sense the heart rhythm. The term non-electrical sensor does not exclude sensors which use electrical or electronic techniques to detect pressure or noise signals. A non-electrical sensor would not detect the stimulation impulse and consequently only trigger on the following P-wave or QRS complex, depending on whatever non-electrical sensing system is being used.

This sensor would not necessarily replace the ECG sensing in this invention, because the ECG display is being used to adjust the delay to the wanted time relative to the ECG (window of 5% before and 45% of R-R after the end of T-wave).

Figure 9:
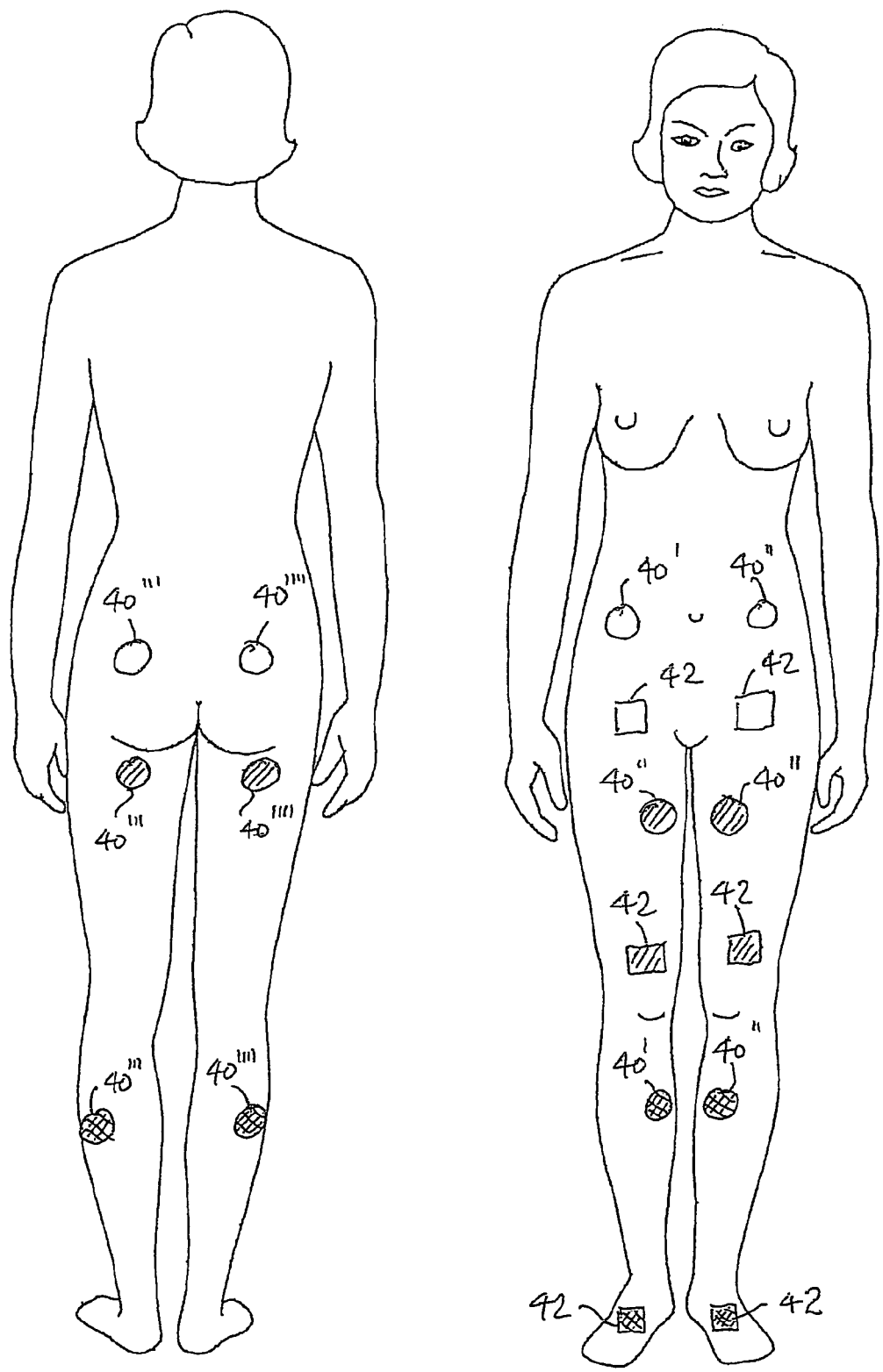
FIG. 9 is a diagram illustrating one possible placement of active electrodes on a person.

Turning now to FIG. 9 there is shown a person who has been provided with a variety of electrodes 40', 40'', 40''', 40'''' and corresponding passive electrodes 42. The electrodes shown as circles with a white interior are associated with a group A of four channels. The circular electrodes with single hatching are associated with a group B of four channels and the four electrodes with cross-hatching are associated with group C of four channels. The passive electrodes 42 associated with each group of channels are shown as squares. They are electrically equivalent and are unhatched for channel group A, single-hatched for channel group B and cross-hatched for channel group C.

The electrodes 40' and 40'' of group A are provided over the left and right lateralis groups of muscles. The electrodes 40''' and 40'''' of the group A are provided over the left and right glutea muscles. The passive electrodes 42 associated with group A are placed over the infra inguinalis muscles.

The electrodes 40' and 40'' of group B are provided over the left and right femoralis medialis muscles whereas the electrodes 40''' and 40'''' associated with group B are provided over the left and right sulcus gluteallis muscles. The passive electrodes associated with channel group B are provided over the left and right supragenus muscles.

The electrodes 40' and 40'' associated with channel group C are provided over the left and right medialio muscles whereas the electrodes 40''' and 40'''' are provided over the left and right lateralis muscles of the calf. The passive electrodes 42 associated with channel group C are provided over the doralis pedis muscles on the left and right feet of the person.

Thus, in this embodiment the circular non-hatched electrodes 40' to 40'''' and the associated passive electrodes 42 are associated with the regio abdominis/glutea muscles. The single-hatched electrodes 40' to 40''' and the associated single-hatched passive electrodes 42 are associated with the regio glutea-femoralis muscles.

The double-hatched electrodes 40' to 40'''' and the cross-hatched passive electrodes 42 are associated with the regio cruralis muscles.

There are several main ways of operating the electrotherapy apparatus with a patient provided with the electrodes as shown.

Figure 10:
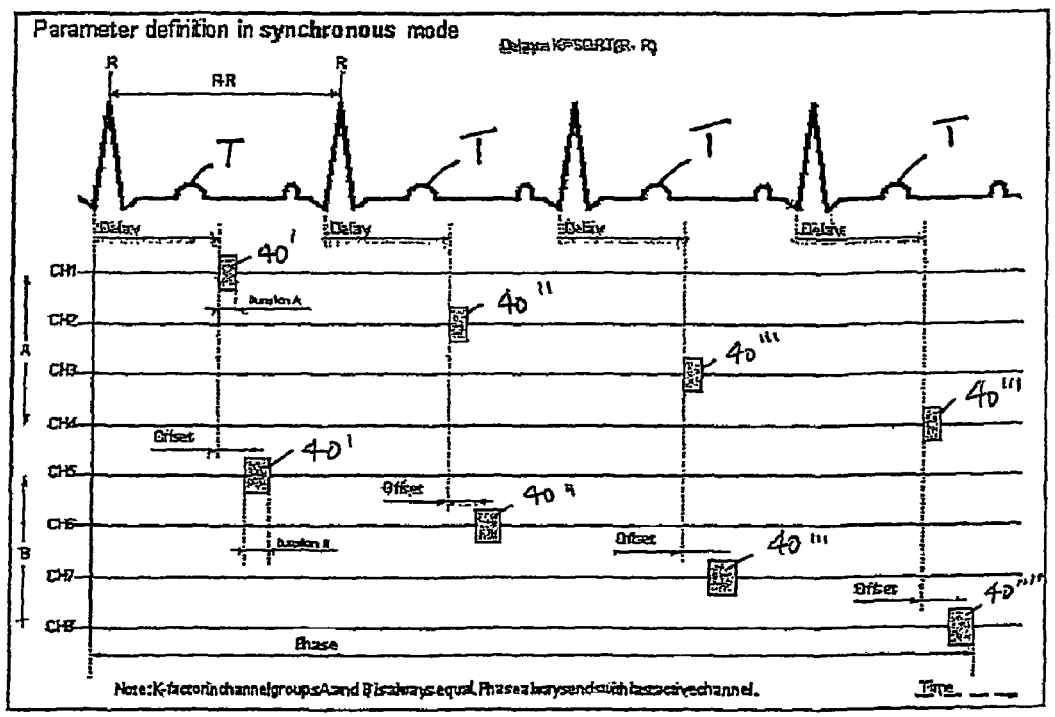
FIG. 10 is a diagram to explain how the electrodes of FIG. 9 can be supplied with stimulation signals.

Before explaining how the electrotherapy apparatus of the invention is used in connection with FIG. 9 it is helpful to consider FIG. 10. This shows how, for the channel group A comprising channels 1 to 4, which are associated with the non-hatched electrodes 40' to 40'''' of FIG. 9, the initial stimulating pulses 44 are applied from channel 1 to electrode 40', from channel 2 to electrode 40'', from channel 3 to electrode 40'''' and from channel 4 to electrode 40'''', in each case at a time just after the end of the T-wave. Moreover it shows how, for the channel group B, comprising the channels 5, 6, 7 and 8, the initial stimulating signals transmitted by those channels are transmitted later than the initial stimulating signals transmitted by the corresponding channels of channel group B by an amount labeled offset. These signals are applied in the scheme of FIG. 9 to the single-hatched electrodes 40' to 40''''. Not shown in FIG. 10 is the channel group C comprising channels 9 to 12 which is associated with the cross-hatched electrodes 40' to 40'''' and where the electrical stimulating signals are provided with an offset which is twice the value of the offset of the signals of channel B (the value twice is chosen arbitrarily and although preferred in this case is not to be understood to be restrictive). As before, the initial electrical stimulation is increased by further stimulating pulses with the aim of terminating the muscle contraction in each heart cycle just before the next R peak. Because the in initial stimulating signals start later in channels B and C than in channel A the total length of muscle contraction of the muscles associated with channels B and C will also be shorter than the muscle contraction associated with channel A, and indeed generally by the amount of the respective offset.

When the electrotherapy apparatus is operated in this mode then the effect will be to increase the pumping of blood from the heart to the periphery. This will lead to improved peripheral arterial perfusion and expediently also to an increase of venous return.

Another possibility exists of exploiting the electrodes in the arrangement shown in FIG. 9. In this case the electrodes are connected differently to the electrotherapy apparatus. More specifically, the non-hatched electrodes 40' to 40'''' are connected to channels 9 to 12 of channel group C. The single-hatched electrodes 40' to 40'''' are connected to channels 5 to 8 of channel group B and the cross-hatched electrodes 40' to 40'''' are connected to the channels 1 to 4 of channel group A. In each case only one channel is connected to any one electrode (as in the previous example).

With the electrodes connected in this way, and operating with the same offsets as shown in FIG. 10, i.e. with the stimulation signals being applied to the channels of channel group A at the end of the T-wave (or shortly thereafter) with the stimulation signals of channel group B being applied to respective electrodes at a later time with a suitable offset value, and with the stimulation signals of channel group C being applied to the associated electrodes with a larger offset time, the effect is to direct blood flow from the periphery back to the heart.

A similar effect can be achieved with only two channel groups A and B, by placing the electrodes of the channel group A either in the region cruralis or region glutea-femoralis and the electrodes of channel group B in the area of the region glutea-femoralis or region abdominis/glutea. Essential is that the electrodes of the different groups are close in body areas which have a significant difference in their distance from the heart. To direct the effect from the periphery to the heart, the electrodes of the channel group stimulating later (due to the offset) are placed closer to the heart than the ones from the channel group stimulating earlier.

Alternatively, it is possible operate with no offset between the channel groups A and B, or A and B and C, if three groups of channels are provided.

The apparatus used to trigger the electrical stimulation pulses can be the apparatus described in the simultaneously filed European patent application entitled "Electrotherapy Apparatus And Method Of Treating A Person Or A Mammal Using Such Electrotherapy Apparatus", application Ser. No. 10/578,585, which was published on Aug. 23, 2007 as US 2007/0198064 A1, which is incorporated herein by reference.

Turning now to FIGS. 11A to 11L there can be seen a series of drawings which show examples of the individual pulse trains or pulse groups identified by the reference numerals 1, 2, 3, . . . n in FIGS. 6 and 7. It should be stressed that these drawings are purely by way of example to explain possible realizations of the invention and possible variations of the pulse trains or groups, but should in no way be understood as being to scale or to restrict the present invention. Also there is no specific restriction to the number of pulses in any one pulse group 1, 2, 3, 4, . . . n, to the pulse repetition frequency of the pulses in any one pulse group, or to the intervals between sequential pulses of any pulse group or between sequential pulse groups, or to the amplitudes of individual pulses or of the individual pulse groups. Equally it is not essential that the amplitude of each negative half wave of a pulse is the same as the amplitude of the positive half wave, although this is generally desirable from the point of view of the net electrical loading of the human or animal body.

Figure 11A:
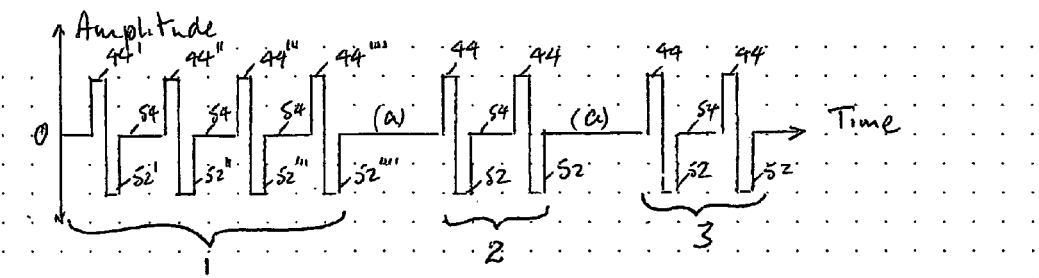
FIGS. 11A to 11L are diagrams similar to FIG. 5 but showing alternative possibilities for the pulse trains.
Figure 11B:
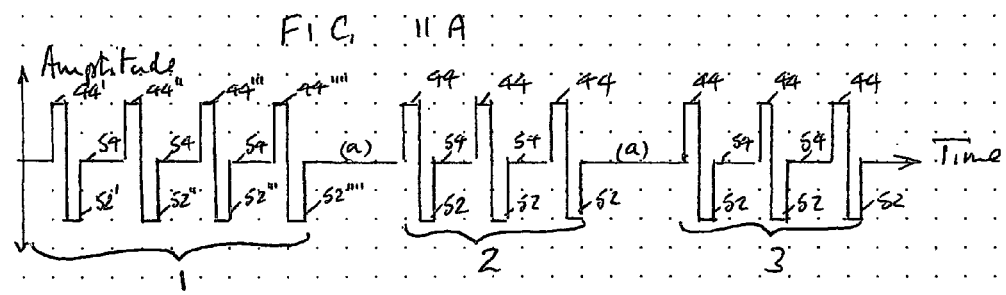
Figure 11C:
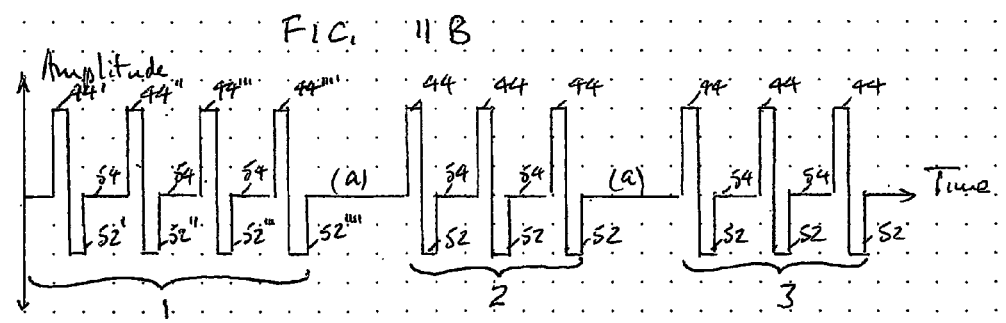
Figure 11D:
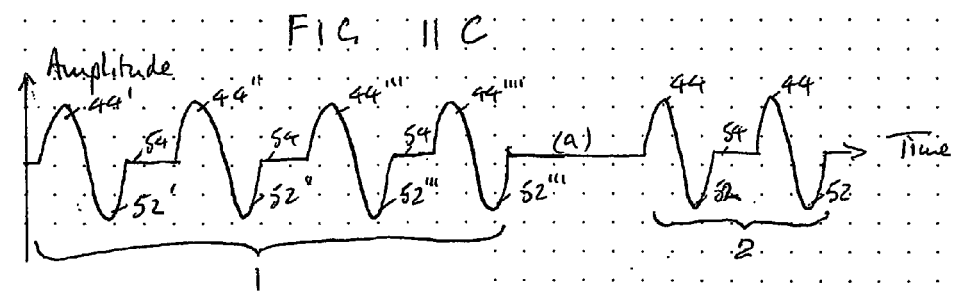
Figure 11:
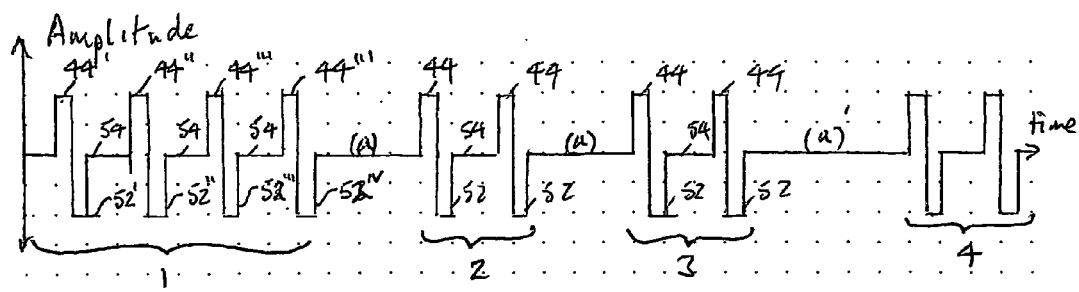
Figure 11:
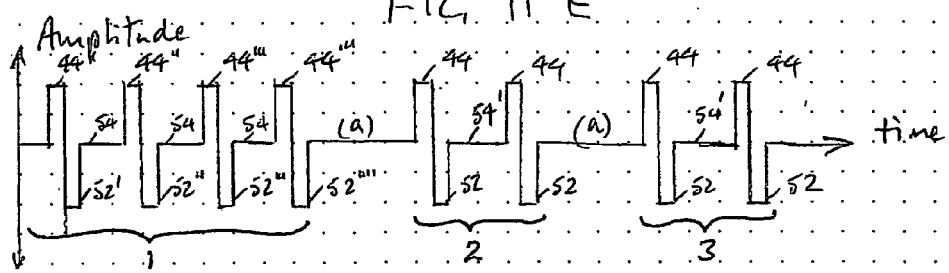
Figure 11:
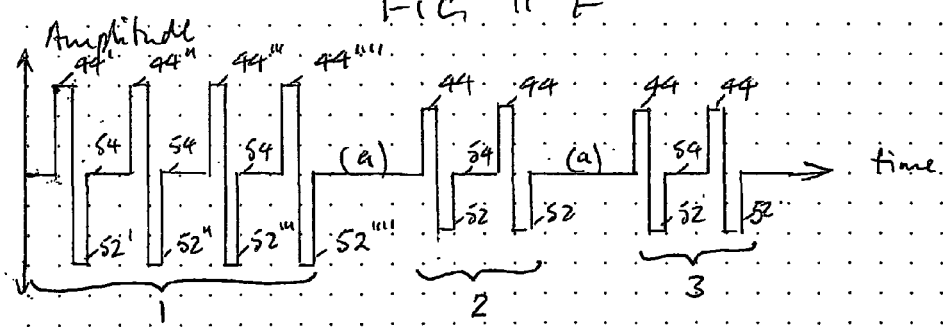
Figure 11:
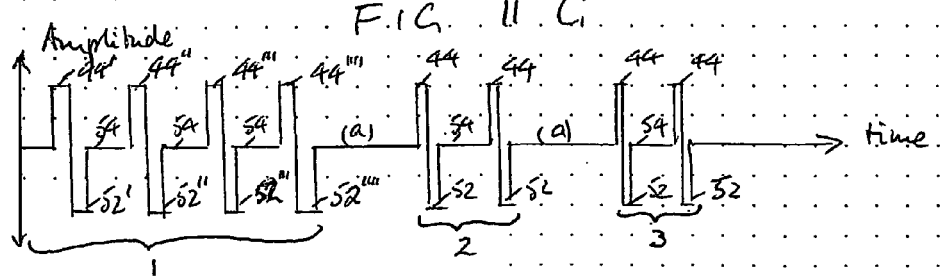

It should also be noted that to simplify the illustration, generally only the first pulse train or group 1 and the second and third pulse trains or groups are shown, in the case of FIG. 11D the pulse group 3 is omitted and in the case of FIG. 11E the pulse group 4 is also shown. There can however be additional pulse groups 4, 5, . . . n and generally speaking there will be additional pulse groups 4, 5, . . . n as suggested in FIGS. 6 and 7 and it will be understood that these additional pulse groups will normally be repeats of the previous pulse groups 2 and 3 (where shown) and will generally repeat the pattern of or continue the development of the pattern set by the earlier pulse groups 2, 3, etc. It is however also possible for the pattern of additional pulse groups to differ from the pattern of the earlier pulse groups 2, 3, etc., or for them not to form a development of the earlier pulse groups. The later pulse groups 4, 5, . . . n of any of the examples given could, for example, be chosen from the pulse groups of any of the other examples given or could be chosen independently of any of the examples given.

It should also be appreciated that in all the examples 11A to 11L the first pulse group 1 is shown as having four individual pulses. This is again not essential. There could be more pulses or fewer pulses, e.g. five pulses as shown at 44', 44'', 44''', 44'''' and 44''''' in FIGS. 5A and B. Also the intervals 54 between the individual pulses could be constant or differ.

In the example of FIG. 11A the first pulse group 1 has a fixed pulse repetition frequency and a pulse duration which is shorter than the period of the pulse repetition frequency so that the interval 54 between successive pulses 44', 52'; 44'', 52''; 44''', 52'''; 44'''', 52'''' is greater than the duration of a single pulse 44', 52'; 44'', 52''; 44''', 52'''; or 44'''', 52'''' of the first pulse group 1. The first pulse group 1 is followed by an interval (a) greater than the period of one cycle of the pulses of the first pulse group 1 (duration of one pulse 44', 52'; 44'', 52''; 44''', 52'''; or 44'''', 52''''+interval 54). This first pulse group 1 is followed after the interval (a) by a second pulse group 2 comprising, in this embodiment, two pulses 44, 52 which are identical to the pulses 44', 52'; 44'', 52''; 44''', 52'''; and 44'''', 52'''' of the first pulse group 1, i.e. have the same amplitude and pulse repetition frequency and the same interval 54 as the pulses of the first group 1. The third pulse group 3 (and any further pulse groups that are provided) follows the second pulse group 2 after the same interval (a) and is identical to the second pulse group 2.

The pulse sequence of FIG. 11B is closely similar to that of FIG. 11A as the reference numerals and letters show. It will be understood that the same description applies in all embodiments to all parts and pulses having the same reference numbers and letters unless something is stated to the contrary. In fact the only difference between the pulse sequence of FIG. 11B and that of FIG. 11A is that each of the pulse groups 2, 3, . . . n comprises three individual pulses rather than two as in FIG. 11A.

The pulse sequence of FIG. 11C is again closely similar to that of FIG. 11B, the only difference being that the amplitude of the positive half pulses 44', 44", 44''' and 44'''' as well as that of pulses 44 is greater than the amplitude of the corresponding pulses in FIG. 11B and greater than that of the negative half impulses 52', 52", 52''' and 52'''' as well as 52. However the negative half pulses such as 52 could also be of higher negative amplitude, e.g. equal to the amplitude of the positive half pulses such as 44, or could be of higher (negative) amplitude than the positive half pulses 44.

In FIG. 11D the pulse sequence is again closely similar to that of FIG. 11A except that the individual pulses 44', 52'; 44", 52"; 44''', 52'''; and 44'''', 52'''' as well as 44, 52 are sinusoidal pulses rather than rectangular wave pulses.

The sequence of pulses shown in FIG. 11E is similar to that of FIG. 11A except that the interval (a)' between the third and fourth pulse groups 3, 4 has increased. This illustration is meant to show that the interval (a) between successive pulse groups can increase, e.g. progressively between each successive pair of pulse groups such as 2, 3 and 3, 4 or simply between certain pairs of successive pulse groups, e.g. 3, 4 as in this example.

The sequence of pulses of FIG. 11F is again similar to that of FIG. 11A except that here the interval 54' between successive pulses 44, 52 of the pulse groups 2, 3, etc. is greater than the interval 54 between the individual pulses 44', 52'; 44", 52"; 44''', 52'''; and 44'''', 52'''' of the first group 1.

The embodiment of FIG. 11G is again similar to that of FIG. 11A except that the amplitude of the second, third and any subsequent pulse groups 2, 3, . . . n is lower than that of the first pulse group 1. In order to prolong the contraction it may however be appropriate to increase the amplitude of at least one subsequent pulse group, e.g. of pulse group 4 (not shown).

FIG. 11H shows another possible variant of the pulse sequence of FIG. 11A in which the amplitude and pulse interval of the second and third pulse groups 2, 3 (and of any subsequent pulse group 4, . . . n) is essentially constant but the duration of each pulse 44, 52 of the second group 2 is less than that of each pulse 44', 52'; 44", 52"; 44''', 52'''; or 44'''', 52'''' of pulse group 1 and the duration of each pulse of pulse group 3 is less than that of each pulse of pulse group 2, etc. It would however also be possible for the pulse duration of the pulse group 3 and of subsequent pulse groups 4, . . . n to be the same as that of pulse group 2.

Figure 11I:
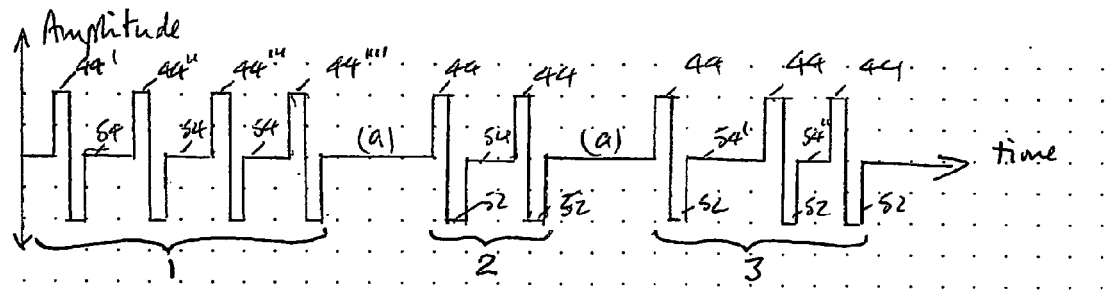

The pulse diagram of FIG. 11I shows that the number of individual pulses in sequential groups 2, 3, . . . n need not necessarily be the same but could, e.g. increase, as can be seen from the fact that pulse group 3 contains three individual pulses 44, 52 whereas pulse group 2 has only two individual pulses. Moreover, FIG. 11I shows, with respect to the pulse group 3, that the pulse interval between individual pulses of the group need not be constant.

Figure 11J:
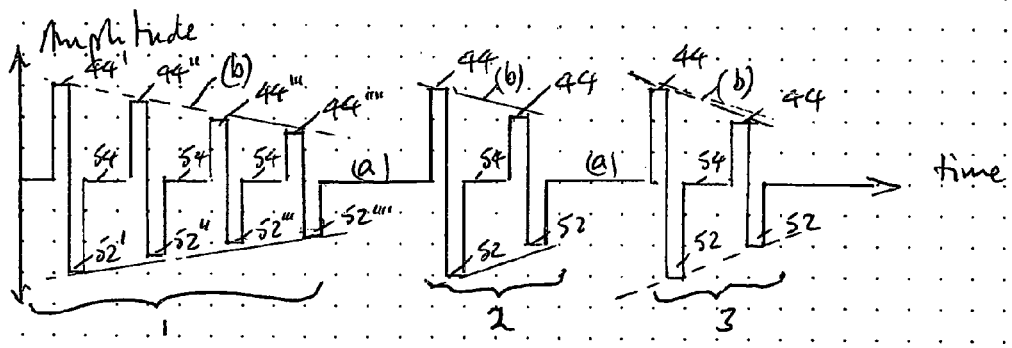

The diagram of FIG. 11J shows that the amplitude of the individual pulses 44', 52'; 44", 52"; 44''', 52'''; 44'''', 52''''; 44, 52; 44, 52 of the individual pulse groups 1, 2, 3 . . . n need not be constant but could vary, e.g. could decrease with a constant slope in accordance with curve (b).

Figure 11K:
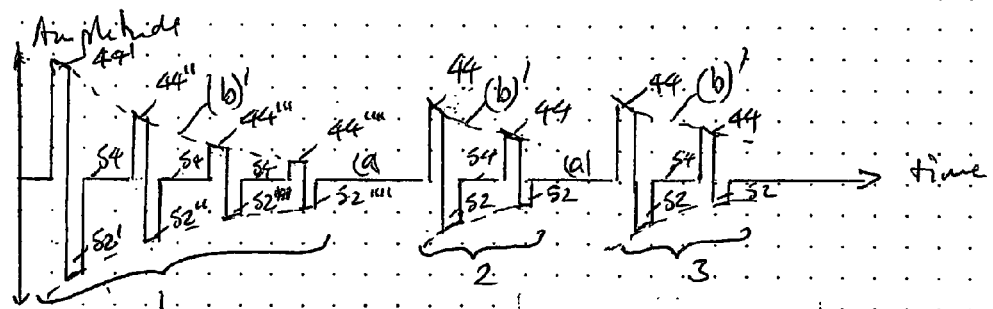

The diagram of FIG. 11K is basically similar to that of FIG. 11J but shows that the decrease in amplitude need not be linear (curve (b)') but could, for example, also be degressive.

Figure 11L:
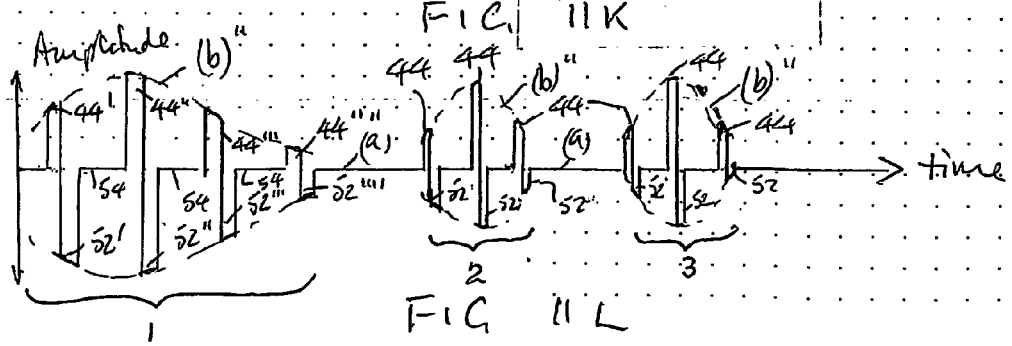

Finally FIG. 11L shows that the variation in amplitude of the pulses 44', 52'; 44", 52"; 44''', 52'''; 44'''', 52''''; 44, 52; 44, 52 of any pulse group 1, 2, 3, . . . n respectively could follow a non-linear function, for example, first increasing and then decreasing as shown by the sinusoidal envelope curves (b)' in FIG. 11L. FIG. 11L also shows that the pulse duration of the pulses in the subsequent pulse groups 2, 3, . . . n can easily be selected to be less than (or greater than) that of the pulses of the first pulse group 1.

The invention claimed is:

1. An electrotherapy apparatus comprising a sensor for detecting periodically recurring signal peaks, in particular the R-R peaks of an electrocardiogram of a person, a processor for deriving from a time interval between said periodically recurring signal peaks a time delay corresponding to approximately the end of the T-wave, one or more active electrodes, a trigger system initiated by an output signal of said processor or embodied within said processor for applying a train of electrical stimulation pulses to the one or more active electrodes provided on the said person at a time related to the end of said time delay, wherein the processor is adapted to generate, for each R-R period of a heart rate, a first train of electrical stimulation pulses having a first pulse repetition frequency and a first interval between successive pulses to induce an initial muscle contraction, and a plurality of further electrical stimulation pulses or groups of electrical stimulation pulses, said further electrical stimulation pulses or groups of electrical stimulation pulses being generated at intervals longer than said first interval between the pulses of the first train of electrical stimulation pulses, so that said further electrical stimulation pulses or groups of electrical simulation pulses maintain said muscle contraction with a reduced energy input, said apparatus being adapted to apply said further electrical stimulation pulses or groups of electrical stimulation pulses to said person over a period extending from said first train of electrical stimulation pulses up to a time just before a next expected R-peak, and wherein said processor is adapted to terminate said further electrical stimulation pulses at a time such that said muscle contraction finishes in a calculated window of 85% to 95% of the preceding R-R path length, or of an average value of the preceding R-R path length, after the last R-peak.

2. An electrotherapy apparatus in accordance with claim 1, wherein the processor is adapted to make a determination for successive pairs of signal peaks received from said sensor of a value corresponding to the time interval between said successive pairs of signal peaks and thus to the said person's momentary heart rate.

3. An electrotherapy apparatus in accordance with claim 1, wherein said processor is adapted to generate said first train of electrical stimulation pulses at a time in the range from −5% of the preceding R-R path length, or of an average value of the preceding R-R path lengths, before the expected end of the T-wave and 45% of the preceding R-R path length, or of an average value of the preceding R-R path lengths, after the expected end of the T-wave.

4. An electrotherapy apparatus in accordance with claim 1, wherein the first train of electrical stimulation pulses comprises a plurality of biphasic signal pulses.

5. An electrotherapy apparatus in accordance with claim 4, wherein the first train of electrical stimulation pulses comprises from 2 to 10 individual pulses having a first pulse repetition frequency in the range from 50 to 250 Hz.

6. An electrotherapy apparatus in accordance with claim 5, wherein the first pulse repetition frequency is in the range from 100 to 200 Hz.

7. An electrotherapy apparatus in accordance with claim 5, wherein the first pulse repetition frequency is 150 Hz.

8. An electrotherapy apparatus in accordance with claim 4, wherein said further pulses have a pulse repetition frequency in the range from 20 to 80 Hz.

9. An electrotherapy apparatus in accordance with claim 8, wherein the pulse repetition frequency is in the range from 30 to 50 Hz.

10. An electrotherapy apparatus in accordance with claim 8, wherein the pulse repetition frequency is 40 Hz.

11. An electrotherapy apparatus in accordance with claim 1, wherein the pulses of said first train of electrical stimulation pulses have a pulse width lower than a pulse interval between said pulses.

12. An electrotherapy apparatus in accordance with claim 11, wherein said pulses of said first train of electrical stimulation pulses have a pulse width of the order of magnitude of 1 ms and the pulse intervals between the said pulses have a duration of the order of magnitude of 3 to 10 ms.

13. An electrotherapy apparatus in accordance with claim 1, wherein said further stimulating pulses are single biphasic pulses.

14. An electrotherapy apparatus in accordance with claim 1, wherein the pulse interval between said further electrical stimulation pulses lies in the range from 15 to 45 ms.

15. An electrotherapy apparatus in accordance with claim 1, wherein the interval between said further electrical stimulation pulses is selected to be greater than an interval between a signal being initiated at said sensor by a new R-peak and a time delay until this signal has been processed by said processor.

16. An electrotherapy apparatus in accordance with claim 1, wherein the processor is adapted to terminate said further electrical stimulation pulses at a time in the range from 70 to 90% of the preceding R-R path length, or of an average value of the preceding R-R path length, after the last detected R-peak.

17. An electrotherapy apparatus in accordance with claim 1, wherein on detection of a next R-peak earlier than the expected time corresponding to the preceding R-R path length since the last R-pulse, or corresponding to an average value of the preceding R-R path lengths since the last R-pulse, the processor is adapted to inhibit any further electrical stimulation pulse until a time after the projected end of the T-wave in a subsequent heart cycle.

18. An electrotherapy apparatus in accordance with claim 1, wherein the processor is adapted to vary the pulse repetition frequency of the first train of electrical stimulation pulses in accordance with a predetermined pattern or randomly within a specified frequency range.

19. An electrotherapy apparatus in accordance with claim 1, wherein the processor is adapted to vary the pulse repetition frequency of the further electrical stimulation pulses in accordance with a predetermined pattern or randomly within a specified frequency range.

20. An electrotherapy apparatus in accordance with claim 1, wherein said processor is adapted to vary an amplitude of pulses comprising said first train of electrical stimulation pulses and/or of said further electrical stimulation pulses in accordance with a predefined pattern or randomly within a pre-specified range.

21. An electrotherapy apparatus in accordance with claim 1, wherein the processor is adapted to vary the shape of pulses comprising said first train of electrical stimulation pulses and of said further pulses.

22. An electrotherapy apparatus in accordance with claim 1, wherein said sensor comprises an electrocardiograph and said processor is provided with a gating program to inhibit recognition of supposed R-peaks from said electrocardiograph in time intervals corresponding to the transmission of said first train of electrical stimulation pulses and of said further electrical stimulation pulses.

23. An electrotherapy apparatus in accordance with claim 1, wherein said sensor is a non-electric sensor, or a non-electric sensor used in addition to an electrocardiograph.

24. An electrotherapy apparatus in accordance with claim 23, wherein said non-electric sensor is selected from the group comprising a non-invasive, aortic pressure measurement device, an invasive aortic pressure measurement device and a noise detection device adapted to detect the closing of the heart valves.

25. An electrotherapy apparatus in accordance with claim 1, wherein the apparatus has a plurality of output channels for applying electrical stimulations to a plurality of active electrodes provided on the said person.

26. An electrotherapy apparatus in accordance with claim 25, wherein a plurality (Y) of channel groups (A, B; A, B, C) is provided, each channel group (A, B; A, B, C) comprising a plurality of channels.

27. An electrotherapy apparatus in accordance with claim 26, wherein each channel group (A, B; A, B, C) has the same number of channels (Ch.1, Ch. 2, Ch. 3, Ch.4 (Group A); Ch. 5, Ch. 6, Ch. 7, Ch. 8 (Group B); Ch. 9, Ch. 10, Ch. 11, Ch. 12 (Group C)).

28. An electrotherapy apparatus in accordance with claim 27, wherein means are provided for providing each channel group (A, B; A, B, C) with the same time delay.

29. An electrotherapy apparatus in accordance with claim 27, wherein means are provided for providing each channel group (A, B; A, B, C) with a respective time delay generally different from time delays associated with other channel groups.

30. An electrotherapy apparatus in accordance with claim 29, wherein the processor is adapted to provide a said time delay for one group of channels (A) and to add a respective time offset to said time delay for each further channel group (B; B, C).

31. An electrotherapy apparatus in accordance with claim 1, wherein said further electrical stimulation pulses each comprise a train of pulses, the pulses of each train being separated by an interval or following one another directly, thereby defining a duration of each train.

32. An electrotherapy apparatus in accordance with claim 31, wherein intervals are present between the initial electrical stimulation and the first train and between sequential trains.

33. An electrotherapy apparatus in accordance with claim 31, wherein the pulses in any train can have amplitudes of any desired level and different amplitudes within the same train and/or the duration of each train can be different from the duration of any other train and/or the pulse repetition frequency of the pulses in any one train can be different and can differ from train to train.

* * * * *